United States Patent
Gryaznov et al.

(10) Patent No.: US 6,608,036 B1
(45) Date of Patent: Aug. 19, 2003

(54) OLIGONUCLEOTIDE N3'→P5' THIOPHOSPHORAMIDATES: THEIR SYNTHESIS AND ADMINISTRATION TO TREAT NEOPLASMS

(75) Inventors: Sergei Gryaznov, San Mateo, CA (US); Krisztina Pongracz, Oakland, CA (US); Tracy Matray, San Lorenzo, CA (US)

(73) Assignee: Geron Corporation, Menlo Park, CA (US)

( * ) Notice: Subject to any disclaimer, the term of this patent is extended or adjusted under 35 U.S.C. 154(b) by 152 days.

(21) Appl. No.: 09/657,445

(22) Filed: Sep. 8, 2000

Related U.S. Application Data
(60) Provisional application No. 60/153,201, filed on Sep. 10, 1999, and provisional application No. 60/160,444, filed on Oct. 19, 1999.

(51) Int. Cl.$^7$ .............................................. A61K 31/70
(52) U.S. Cl. ........................ 514/44; 536/23.1; 536/24.3; 536/24.5; 435/6
(58) Field of Search ........................... 514/44; 536/23.1, 536/24.3, 24.5; 435/6

(56) References Cited

U.S. PATENT DOCUMENTS

| | | | |
|---|---|---|---|
| 4,647,529 A | 3/1987 | Rodland et al. ................. | 435/6 |
| 5,476,925 A | 12/1995 | Letsinger et al. ........... | 536/23.1 |
| 5,506,212 A | 4/1996 | Hoke et al. .................... | 514/44 |
| 5,583,016 A | 12/1996 | Villeponteau et al. ...... | 435/91.3 |
| 5,591,607 A | 1/1997 | Gryaznov et al. .......... | 435/91.1 |
| 5,631,135 A | 5/1997 | Gryaznov et al. ............. | 435/6 |
| 5,645,986 A * | 7/1997 | West et al. ..................... | 435/6 |
| 5,684,143 A | 11/1997 | Gryaznov et al. .......... | 536/23.1 |
| 5,776,679 A | 7/1998 | Villeponteau et al. ......... | 435/6 |
| 5,824,793 A | 10/1998 | Hirschbein et al. ....... | 536/25.34 |
| 5,837,857 A | 11/1998 | Villeponteau et al. ... | 536/24.31 |
| 5,856,096 A * | 1/1999 | Windle et al. .................. | 435/6 |
| 5,958,680 A | 9/1999 | Villeponteau et al. ......... | 435/6 |
| 5,968,506 A * | 10/1999 | Weinrich et al. ............ | 424/94.5 |
| 5,972,605 A | 10/1999 | Villeponteau et al. ......... | 435/6 |
| 6,004,939 A | 12/1999 | Chen et al. .................... | 514/43 |
| 6,015,710 A * | 1/2000 | Shay et al. .................. | 435/375 |
| 6,017,895 A | 1/2000 | Cook ........................... | 514/44 |
| 6,046,307 A * | 4/2000 | Shay et al. .................. | 530/324 |
| 6,054,575 A * | 4/2000 | Villeponteau et al. ... | 536/24.31 |
| 6,258,535 B1 | 7/2001 | Villeponteau et al. ......... | 435/6 |
| 6,320,039 B1 | 11/2001 | Villeponteau et al. ... | 536/24.31 |
| 6,342,358 B1 | 1/2002 | Collins et al. ................. | 435/6 |

FOREIGN PATENT DOCUMENTS

| | | |
|---|---|---|
| DE | 19720151 A1 * | 11/1998 |
| EP | 0 751 948 B1 | 9/2002 |
| JP | 11-228451 A2 * | 8/1998 |
| WO | WO 95/25814 | 9/1995 |
| WO | WO 96/01835 A1 | 1/1996 |
| WO | WO 97/31009 | 8/1997 |
| WO | WO 97/37691 | 10/1997 |
| WO | WO 98/11207 A2 | 3/1998 |
| WO | WO 98/50397 A2 * | 11/1998 |
| WO | WO 01/74136 A2 | 10/2001 |

OTHER PUBLICATIONS

Zobkiw, L, "Studies Demonstrate Significant Anti–tumor Activity Against Human Myeloma and Lymphoma Tumors in Mice; In Vivo Data Add to Growing Evidence of Tolomerase Inhibition as a Potential Treatment for Cancer," Press Release, Geron Corporation, Menlo Park, CA, Jun. 13, 2002, four page document.*

Shea–Herbert et al., "Oligonucleotide N3'–>P5' Phosphoramidates as Efficient Telomerase Inhibitors," *Oncogene*, 21, 638–642 (2002).*

Glukhov et al., "Inhibition of Telomerase Activity of Melanoma Cells In Vitro by Antisense Oligonucleotides," *Biochemical and Biophysical Research Communications*, 248(2), 368–371 (Jul. 20, 1998).*

Pitts et al., "Inhibition of Human Telomerase by 2'–O–methyl–RNA," *Proceeding of the National Academy of Sciences USA*, 95, 11549–11554 (Sep. 29, 1998).*

Tao et al. (I), "Specific Inhibition of Human Telomerase Activity by Transfection Reagent, FuGENE6–Antisense Phosphorothioate Oligonucleotide Complex in HeLa Cells," *FEBS Letters*, 454(3), 312–316 (Jul. 9, 1999).*

Tao et al. (II), "Inhibition of Telomerase Activity of Antisense Oligo–nucleotides in HeLa Cells," *Twentyfifth Symp. on Nucleic Acids Chemistry, Nucleic Acids Symposium Series*, No. 39, pp. 85–86, Sugitomo et al. (eds.), Oxford University Press, Kobe, Japan, Sep. 18–20, 1998.*

Gryaznov, S., et al.., "Oligonucleotides N3'→P5' Phosphoramidates As Antisense Agents", Nucleic Acids Res., 24(8):1508–1514 (1996), (Apr. 15, 1996).

Hamilton, S., et al., "Cellular Delivery of Peptide Nucleic Acids and Inhibition of Human Telomerase", Chemistry & Biology, 6:343–351 (May 12, 1999).

Kers, I., et al., "A New Synthetic Method for the Preparation of Nucleoside Phosphoramidate Analogues with the Nitrogen Atom in Bridging Positions of the Phosphoramidate Linkage", Tetrahedron Ltrs., 39:1219–1222 (1998).

Mignet, N., et al., "Zwitterionic Oligodeoxyribonucleotide N3'→P5' Phosphoramidates: Synthesis and Properties", Nucleic Acids Research, 26(2):431 (1998), (Issue No. 2).

Ohnuma, T., et al., "Inhibitory Effects of Telomere–Mimic Phosphorothioate Oligonucleotides on Various Human Tumor Cells In Vitro", Anticancer Research, 17:2455–2458 (1997).

(List continued on next page.)

Primary Examiner—James O. Wilson
Assistant Examiner—Lawrence E Crane
(74) Attorney, Agent, or Firm—Geron Corporation

(57) ABSTRACT

Oligonucleotides with a novel sugar-phosphate backbone containing at least one internucleoside 3'-NHP(O)(S⁻)O-5' linkage, and methods of synthesizing and using the inventive oligonucleotides are provided. The inventive thiophosphoramidate oligonucleotides were found to retain the high RNA binding affinity of the parent oligonucleotide N3'→P5' phosphoramidates and to exhibit a much higher acid stability.

19 Claims, 8 Drawing Sheets

OTHER PUBLICATIONS

Testa, S., et al., "In Vitro Suicide Inhibition of Self–Splicing of a Group I Intron from Pneumocystis Carinii by An N3'→P5' Phosphoramidate Hexanucleotide", Proc. Natl. Acad. Sci. USA, 96:2734 (Mar., 1999).

Wagner, R., "Gene Inhibition Using Antisense Oligodeoxynucleotides", Nature, 372:333 (Nov. 24, 1994).

Corey DR, et al., Telomerase inhibition, oligonucleotides, and clinical trials, Oncogene 21:631 (2002).

Folini M, et al., Inhibition of telomerase activity by a hammerhead ribozyme targeting the RNA component of telomerase in human melanoma cells, J Invest Dermatol. 114:259 (Feb. 2, 2000).

Harrison, J, et al., Inhibitionof Human Telomerase by PNA–Cationic Peptide Conjugates, Bioorganic & Med Chem Letters 9:1273 (1999).

Komata T, Combination therapy of malignant glioma cells with 2–5A–antisense telomerase RNA and recombinant adenovirus p53, Gene Ther. 7:2071 (2000).

Matthes, et al., Telomerase Protein Rather Than Its RNA is the Target of Phosphorothioate–Modified Oligonucleotides, Nucleic Acids Res. 27:1152 (1999).

Muller A, et al., Telomerase inhibition by induced expression of antisense RNA, Adv Exp Med Biol. 451:23 (1998).

Saeki T, et al., Inhibitory Effect of Telomere–Mimic Phosphorothioate Oligodeoxy Nucleotides (S–ODNS) on Human Tumor Cell Lines, Oncology 57:27 (Suppl 2) (1999).

Saretzki G, et al., Ribozyme–mediated telomerase inhibition induces immediate cell lose but not telomerase shortening in ovarian cancer cells, Cancer Gene Ther. 8:827 (2001).

Schindler A, et al., Human telomerase reverse transcriptase antisense treatment downregulates the viability of prostate cancer cells in vitro, Int J Oncol. 19:25 (2001).

Shae–Herbert, et al., Oligonucleotide N3'–P5' phosphoramidates as efficient telomerase inhibitors, Oncogene 21:638 (2002).

Shammas M, et al., Telomerase inhibition by peptide nucleic acids reverse 'immortality' of transformed human cells, Oncogene 18:6191 (1999).

Tamura, Y, et al., Inhibition of Human Telomerase Activity by Antisense Phosphorothioate Oligonucleotides Encapsulated with the Transfection Reagent, FuGENE™6, in HeLa Cells, Antisense & Nucleic Acid Drug Dev 10:87 (2000).

Tao M, et al., Specific inhibition of human telomerase activity by transfection reagent, FuGENE6–antisense phosphorothioate oligonucleotide complex in HeLa cells, FEBS Lett. 454:312 (1999).

Villa R, et al., Inhibition of telomerase activity by a cell–penetrating peptide nucleic acit construct in human melanoma cells, FEBS Letters 473:241 (2000).

von Janta–Lipinski, et al., Protein and RNA of Human Telomerase as Targets for Modified Oligonucleotides, Nucleotides & Nucleotides 18:1719 (1999), (Issue No. 6–7).

* cited by examiner

Key:
a = 5'-phosphoramidite-3'-NH-Tr-nucleoside, TetrH
b = Beaucage reagent or $S_8/CS_2$
c = DCA
d = repeat of steps a—c
e = aq.$NH_3$ Inhibition of Telomerase by Oligonucleotide N3′ → P5′ thio-Phosphoramidates on HME50-5E Cell Growth Inhibition of Telomerase by Oligonucleotide N3′ → P5′ thio-Phosphoramidates on HME50-5E Cell Growth Effects of Oligonucleotide N3' → P5' thio-Phosphoramidates on HME50-5E Cell Growth Telomere Shortening in HME50-5E Cells Treated with Oligonucleotide
N3' → P5' *thio* Phosphoramidates Figure 8
IC$_{50}$ Values for In Vitro Inhibition of Telomerase by
Oligonucleotide N3'→P5' *thio* - Phosphoramidate -
TAGGGTTAGACAA

| Cell Type | IC$_{50}$ µM* Lipids | |
|---|---|---|
| | (−) | (+) |
| HME50-5E | 1 | 0.0008 |
| Caki-1 | 1 | <0.001 |
| A431 | 1 | <0.001 |
| ACHN | 0.3 | nd |
| A549 | 0.5 | nd |

SEQUENCE LISTING

<160> NUMBER OF SEQ ID NOS: 9

<210> SEQ ID NO 1
<211> LENGTH: 11
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 1
gttagggtta g                                                              11

<210> SEQ ID NO 2
<211> LENGTH: 13
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 2
tagggttaga caa                                                            13

<210> SEQ ID NO 3
<211> LENGTH: 11
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 3
gttgagtgta g                                                              11

<210> SEQ ID NO 4
<211> LENGTH: 13
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 4
taggtgtaag caa                                                            13

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 5
gtagacctgt taccagaggg ag                                                  22

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 6

-continued

```
ctaaccctaa ctggtaacag gtctac                                          26

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 7
ttagggttag ggttaggg                                                   18

<210> SEQ ID NO 8
<211> LENGTH: 13
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 8
cagttagggt tag                                                        13

<210> SEQ ID NO 9
<211> LENGTH: 11
<212> TYPE: DNA
<213> ORGANISM: Artificial Sequence
<220> FEATURE:
<223> OTHER INFORMATION: Synthetic oligonucleotide with potential
      inhibition activity

<400> SEQUENCE: 9
gattgggatt g                                                          11
```

OLIGONUCLEOTIDE N3'→P5' THIOPHOSPHORAMIDATES: THEIR SYNTHESIS AND ADMINISTRATION TO TREAT NEOPLASMS

CROSS-REFERENCE TO RELATED APPLICATIONS

The application claims priority from U.S. application Ser. No. 60/153,201, filed Sep. 10, 1999, and from U.S. application Ser. No. 60/160,444, filed Oct. 19, 1999, which are herein incorporated by reference in their entirety.

FIELD OF THE INVENTION

The present invention relates to oligonucleotides having a novel sugar-phosphate backbone containing internucleoside 3'-NHP(O)(S⁻)O-5' linkages. More particularly, the present invention is directed to thiophosphoramidate oligonucleotide compositions, their use as diagnostic or therapeutic agents and methods for synthesizing thiophosphoramidate oligonucleotides.

BACKGROUND OF THE INVENTION

Nucleic acid polymer chemistry has played a crucial role in many developing technologies in the pharmaceutical, diagnostic, and analytical fields, and more particularly in the subfields of antisense and anti-gene therapeutics, combinatorial chemistry, branched DNA signal amplification, and array-based DNA diagnostics and analysis (e.g. Uhlmann and Peyman, Chemical Reviews, 90:543–584, 1990; Milligan et al., J. Med. Chem., 36:1923–1937, 1993; DeMesmaeker et al., Current Opinion in Structural Biology, 5:343–355, 1995; Roush, Science, 276:1192–1193, 1997; Thuong et al., Angew. Chem. Int. Ed. Engl., 32:666–690, 1993; Brenner et al., Proc. Natl. Acad. Sci., 89:5381–5383, 1992; Gold et al., Ann. Rev. Biochem., 64:763–797, 1995; Gallop et al., J. Med. Chem., 37:1233–1258, 1994; Gordon et al., J. Med. Chem., 37:1385–1401, 1994; Gryaznov, International application PCT/US94/07557; Urdea et al., U.S. Pat. No. 5,124,246; Southern et al., Genomics, 13:1008–1017, 1992; McGall et al., U.S. Pat. No. 5,412,087; Fodor et al., U.S. Pat. No. 5,424,186; Pirrung et al., U.S. Pat. No. 5,405,783).

Much of this chemistry has been directed to improving the binding strength, specificity, and nuclease resistance of natural nucleic acid polymers, such as DNA. Unfortunately, improvements in one property, such as nuclease resistance, often involve trade-offs against other properties, such as binding strength. Examples of such trade-offs abound: peptide nucleic acids (PNAs) display good nuclease resistance and binding strength, but have reduced cellular uptake in test cultures (e.g. Hanvey et al., Science, 258:1481–1485, 1992); phosphorothioates display good nuclease resistance and solubility, but are typically synthesized as P-chiral mixtures and display several sequence-non-specific biological effects (e.g. Stein et al., Science, 261:1004–1012, 1993); methylphosphonates display good nuclease resistance and cellular uptake, but are also typically synthesized as P-chiral mixtures and have reduced duplex stability (e.g. Mesmaeker et al. (cited above); and so on.

Recently, a new class of oligonucleotide analog has been developed having so-called N3'→P5' phosphoramidate internucleoside linkages which display favorable binding properties, nuclease resistance, and solubility (Gryaznov and Letsinger, Nucleic Acids Research, 20:3403–3409, 1992; Chen et al., Nucleic Acids Research, 23:2661–2668, 1995; Gryaznov et al., Proc. Natl. Acad. Sci., 92:5798–5802, 1995; and Gryaznov et al., J. Am. Chem. Soc., 116:3143–3144, 1994). Phosphoramidate compounds contain a 3'-amino group at each of the 2'-deoxyfuranose nucleoside residues replacing a 3'-oxygen atom. The synthesis and properties of oligonucleotide N3'→P5' phosphoramidates are also described in Gryaznov et al., U.S. Pat. Nos. 5,591,607; 5,599,922; 5,726,297; and Hirschbein et al., U.S. Pat. No. 5,824,793.

The oligonucleotide N3'→P5' phosphoramidates form unusually stable duplexes with complementary DNA and especially RNA strands, as well as stable triplexes with DNA duplexes, and they are also resistant to nucleases (Chen et al., Nucleic Acids Research, 23:2661–2668, 1995; Gryaznov et al., Proc. Natl. Acad. Sci., 92:5798–5802, 1995). Moreover oligonucleotide N3'→P5' phosphoramidates are more potent antisense agents than phosphorothioate derivatives both in vitro and in vivo (Skorski et al., Proc. Natl. Acad. Sci., 94:3966–3971, 1997). At the same time the phosphoramidates apparently have a low affinity to the intra- and extracellular proteins and increased acid liability relative to the natural phosphodiester counterparts (Gryaznov et al., Nucleic Acids Research, 24:1508–1514, 1996). These features of the oligonucleotide phosphoramidates potentially adversely affect their pharmacological properties for some applications. In particular, the acid stability of an oligonucleotide is an important quality given the desire to use oligonucleotide agents as oral therapeutics.

In order to circumvent the above described problems associated with oligonucleotide analogs, a new class of compounds was sought that embodies the best characteristics from both oligonucleotide phosphoramidates and phosphorothioates. The present invention describes the synthesis, properties and uses of oligonucleotide N3'→P5' thiophosphoramidates.

SUMMARY OF THE INVENTION

The compositions and methods of the present invention relate to polynucleotides having contiguous nucleoside subunits joined by intersubunit linkages. In the polynucleotides of the present invention, at least two contiguous subunits are joined by a N3'→P5' thiophosphoramidate intersubunit linkage defined by the formula of 3'-[—NH—P(=O)(—SR)—O—]-5', wherein R is selected from the group consisting of hydrogen, alkyl, aryl and salts thereof. In a preferred embodiment of the invention, R is hydrogen or a salt thereof. The inventive polynucleotides can be composed such that all of the intersubunit linkages are N3'→P5' thiophosphoramidate. Alternatively, the polynucleotides of the invention can contain a second class of intersubunit linkages such as phosphodiester, phosphotriester, methylphosphonate, P3'→N5' phosphoramidate, N3'→P5' phosphoramidate, and phosphorothioate linkages.-

An exemplary N3'→P5' thiophosphoramidate intersubunit linkage has the formula:

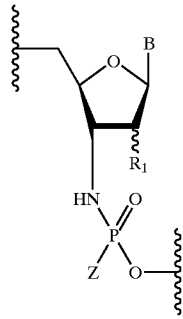

where B is a purine or pyrimidine or an analog thereof, Z is OR, SR, or methyl, wherein R is selected from the group consisting of hydrogen, alkyl, and aryl and their salts; and $R_1$ is selected from the group consisting of hydrogen, O—$R_2$, S—$R_2$, and halogen, wherein $R_2$ is H, alkyl, or $(CH_2)_nW(CH_2)_mH$, where n is between 1–10, m is between 0–10 and W is O, S, or NH, with the proviso that when Z is methyl or OMe, $R_1$ is not H. The nucleoside subunits making up the polynucleotides can be selected to be in a defined sequence: such as, a sequence of bases complementary to a single-strand nucleic acid target sequence or a sequence that will allow formation of a triplex structure between the polynucleotide and a target duplex. The nucleoside subunits joined by at least one N3'→P5' thiophosphoramidate intersubunit linkage, as described above, have superior resistance to acid hydrolysis, yet retain the same thermal stability as compared to oligonucleotides having phosphoramidate intersubunit linkages.

The present invention also includes a method of synthesizing an oligonucleotide N3'→P5' thiophosphoramidate. In this method a first nucleoside 5'-succinyl-3'-aminotrityl-2', 3'-dideoxy nucleoside is attached to a solid phase support. The first nucleoside additionally has a protected 3' amino group. The protected 3' amino group is then deprotected to form a free 3' amino group to which a second nucleoside is added. The free 3' amino group of the first nucleoside is reacted with a 3'-protected aminonucleoside-5'-O-cyanoethyl-N,N-diisopropylaminophosphoramidite monomer to form an internucleoside N3'→P5' phosphoramidite linkage. The internucleaside phosphoramidite group is then sulfurized to form a N3'→P5' thiophosphoramidate internucleaside linkage between the first and second nucleosides.

In another embodiment of the invention, a method is provided for hybridizing a thiophosphoramidate oligonucleotide of the invention to a DNA or RNA target. The thiophosphoramidate polynucleotide comprises a sequence of nucleoside subunits joined by at least one subunit defined by the formula:

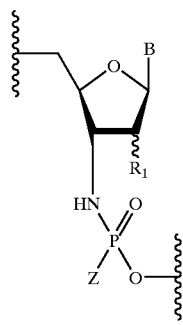

where B is a purine or pyrimidine or an analog thereof, Z is OR, SR, or methyl, and $R_1$ is selected from the group consisting of hydrogen, O—$R_2$, S—$R_2$, and halogen, wherein $R_2$ is H, alkyl, or $(CH_2)_nW(CH_2)_mH$, where n is between 1–10, m is between 0–10 and W is O, S, or NH, with the proviso that when Z is methyl or OMe, $R_1$ is not H. The thiophosphoramidate polynucleotide is contacted with the RNA target to allow formation of a hybridization complex between the polynucleotide and the RNA target.

The present invention also includes pharmaceutical compositions and kits including a polynucleotide having at least one N3'→P5' thiophosphoramidate linkage, as described above. The inventive oligonucleotides are particularly useful in oral therapeutic applications based on hybridization, such as, antigene and antisense applications, including the inhibition of telomerase enzyme activity.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 8 illustrates the $IC_{50}$ values measured for the thiophosphoramidate oligonucleotide SEQ ID NO:2.

DETAILED DESCRIPTION

Definitions

An "alkyl group" refers to an alkyl or substituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$.

An "aryl group" refers to an aromatic ring group having 5–20 carbon atoms, such as phenyl, naphthyl, anthryl, or substituted aryl groups, such as, alkyl- or aryl-substitutions like tolyl, ethylphenyl, biphenylyl, etc. Also included are heterocyclic aromatic ring groups having one or more nitrogen, oxygen, or sulfur atoms in the ring.

Figure 1A:
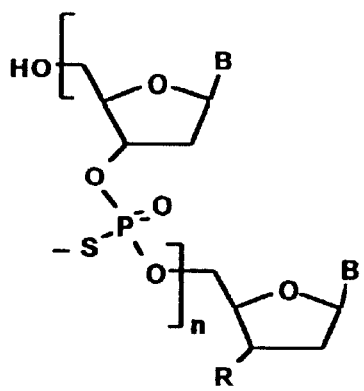
FIG. 1A shows the internucleoside linkage structure of oligonucleotide phosphorothioates.
Figure 1B:
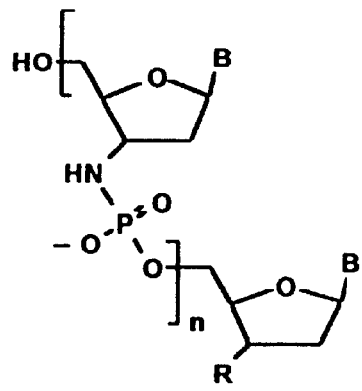
FIG. 1B shows the internucleoside linkage structure of oligonucleotide phosphoramidates.
Figure 1C:
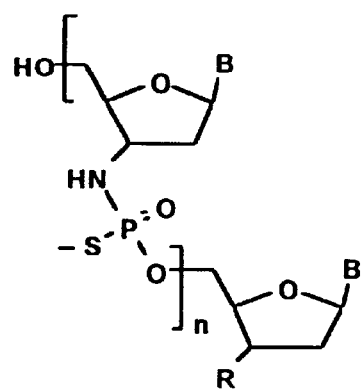
FIG. 1C shows the internucleoside linkage structure of exemplary oligonucleotide thiophosphoramidates of the invention.

"Oligonucleotides" typically refer to nucleoside subunit polymers having between about 3 and about 50 contiguous subunits. The nucleoside subunits can be joined by a variety of intersubunit linkages, including, but not limited to, those shown in FIGS. 1A to 1C. Further, "oligonucleotides" includes modifications, known to one skilled in the art, to the sugar backbone (e.g., ribose or deoxyribose subunits), the sugar (e.g., 2' substitutions), the base, and the 3' and 5' termini. The term "polynucleotide", as used herein, has the same meaning as "oligonucleotide" and is used interchangeably with "polynucleotide".

Whenever an oligonucleotide is represented by a sequence of letters, such as "ATGUCCTG", it will be understood that the nucleotides are in 5'→3' order from left to right.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992), and analogs. "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (Chemical Reviews, 90:543–584, 1990).

A "base" is defined herein to include (i) typical DNA and RNA bases (uracil, thymine, adenine, guanine, and cytosine), and (ii) modified bases or base analogs (e.g., 5-methyl-cytosine, 5-bromouracil, or inosine). A base analog is a chemical whose molecular structure mimics that of a typical DNA or RNA base.

As used herein, "pyrimidine" means the pyrimidines occurring in natural nucleosides, including cytosine, thymine, and uracil, and common analogs thereof, such as those containing oxy, methyl, propynyl, methoxy, hydroxyl, amino, thio, halo, and like, substituents. The term as used herein further includes pyrimidines with common protection groups attached, such as $N_4$-benzoylcytosine. Further common pyrimidine protection groups are disclosed by Beaucage and Iyer (Tetrahedron 48:223–2311, 1992).

As used herein, "purine" means the purines occurring in natural nucleosides, including adenine, guanine, and hypoxanthine, and common analogs thereof, such as those containing oxy, methyl, propynyl, methoxy, hydroxyl, amino, thio, halo, and like, substituents. The term as used herein further includes purines with common protection groups attached, such as $N_2$-benzoylguanine, $N_2$-isobutyrylguanine, $N_6$-benzoyladenine, and the like. Further common purine protection groups are disclosed by Beaucage and Iyer (cited above).

As used herein, the term "-protected-" as a component of a chemical name refers to art-recognized protection groups for a particular moiety of a compound, e.g. "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups include those described in the following references: Gait, editor, Oligonucleotide Synthesis: A Practical Approach (IRL Press, Oxford, 1984); Amarnath and Broom, Chemical Reviews, 77:183–217, 1977; Pon et al., Biotechniques, 6:768–775, 1988; Ohtsuka et al., Nucleic Acids Research, 10:6553–6570, 1982; Eckstein, editor, Oligonucleotides and Analogues: A Practical Approach (IRL Press, Oxford, 1991), Greene and Wuts, Protective Groups in Organic Synthesis, Second Edition, (John Wiley & Sons, New York, 1991), Narang, editor, Synthesis and Applications of DNA and RNA (Academic Press, New York, 1987), Beaucage and Iyer (cited above), and like references.

The term "halogen" or "halo" is used in its conventional sense to refer to a chloro, bromo, fluoro or iodo substituent. In the compounds described and claimed herein, halogen substituents are generally fluoro, bromo, or chloro, preferably fluoro or chloro.

The compounds of the present invention may be used to inhibit or reduce telomerase enzyme activity and/or proliferation of cells having telomerase activity. In these contexts, inhibition or reduction of the enzyme activity or cell proliferation refer to a lower level of the measured activity relative to a control experiment in which the enzyme or cells are not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

The present invention is directed generally to oligonucleotides containing at least one thiophosphoramidate intersubunit linkage, methods of synthesizing such polynucleotides and methods of using the inventive oligonucleotides as therapeutic compounds and to in diagnostics.

The oligonucleotides are exemplified as having the formula:

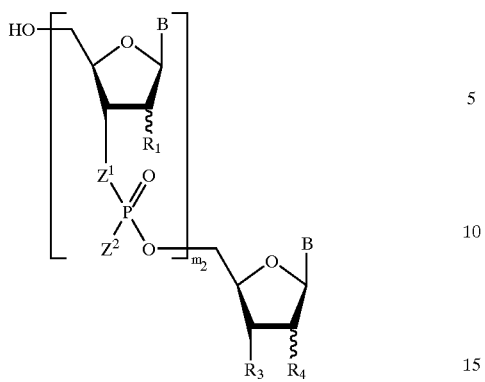

wherein each B is independently selected to be a purine or pyrimidine or an analog thereof such as uracil, thymine, adenine, guanine, cytosine, 5-methylcytosine, 5-bromouracil and inosine, $Z_1$ is O or NH, $Z_2$ is OR, SR, or methyl wherein R is selected from the group consisting of hydrogen, alkyl, aryl and salts thereof, $R_1$ is selected from the group consisting of hydrogen, O—$R_2$, S—$R_2$, NH$R_2$ and halogen, wherein $R_2$ is H, alkyl, or $(CH_2)_nW(CH_2)_mH$, where n is between 1–10, m is between 0–10 and W is O, S, or NH, $R_3$ and $R_4$ are selected from the group consisting of hydroxyl, amino and hydrogen, and $m_2$ is an integer between 1 and 50.

The nucleoside subunits making up the polynucleotides of the present invention can be selected to be in a defined sequence: such as, a sequence of bases capable of hybridizing specifically to a single-strand nucleic acid target sequence or a sequence that will allow formation of a triplex structure between the polynucleotide and a target duplex. Preferably, the sequence of nucleoside subunits are joined by at least one subunit that is a N3'→P5' thiophosphoramidate defined by the formula:

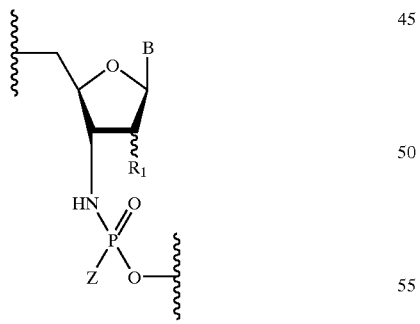

wherein B is a purine or pyrimidine or an analog thereof;

Z is OR, SR, or methyl, wherein R is selected from the group consisting of hydrogen, alkyl, aryl and salts thereof; and $R_1$ is selected from the group consisting of hydrogen, O—$R_2$, S—$R_2$, and halogen, wherein $R_2$ is H, alkyl, or $(CH_2)_nW(CH_2)_mH$, where n is between 1–10, m is between 0–10 and W is O, S, or NH, with the proviso that when Z is methyl or OMe, $R_1$ is not H.

For example, all of the inter-subunit linkages of the polynucleotide can be N3'→P'5 thiophosphoramidate inter-subunit linkages defined by the formula:

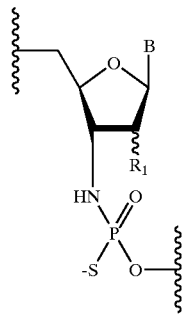

The inventive oligonucleotides can be used to hybridize to target nucleic acid sequences such as RNA and DNA. When desirable, the oligonucleotides of the present invention can be labeled with a reporter group, such as radioactive labels, biotin labels, fluorescent labels and the like, to facilitate the detection of the polynucleotide itself and its presence in, for example, hybridization complexes.

In another aspect of the invention, a kit for isolating or detecting a target RNA from a sample is provided. The kit contains an oligonucleotide having a defined sequence of nucleoside subunits joined by a least one intersubunit linkage defined by the formula:

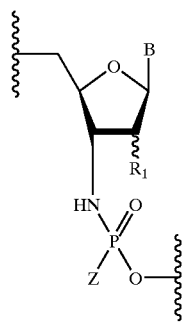

where B is a purine or pyrimidine or an analog thereof; Z is OR, SR, or methyl; and $R_1$ is selected from the group consisting of hydrogen, O—$R_2$, S—$R_2$, and halogen, wherein $R_2$ is H, alkyl, or $(CH_2)_nW(CH_2)_mH$, where n is between 1–10, m is between 0–10 and W is O, S, or NH, with the proviso that when Z is methyl or OMe, $R_1$ is not H, and wherein the oligonucleotide hybridizes to the target RNA.

The oligonucleotides can also be formulated as a pharmaceutical inhibition of transcription or translation in a cell in a disease condition related to overexpression of the target gene.

Preferably, the sequence of nucleoside subunits are joined by at least one inter-subunit linkage that is a N3'→P5' thiophosphoramidate. Alternatively, all of the inter-subunit linkages of the polynucleotide are N3'→P'5 thiophosphoramidate inter-subunit linkages defined by the formula:

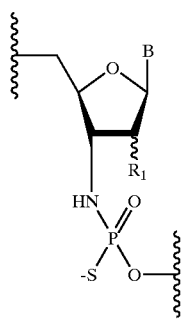

Figure 2:
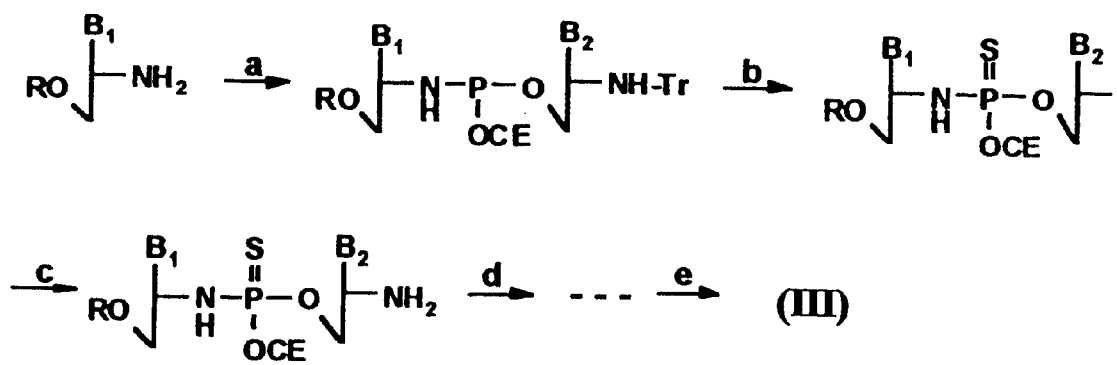
FIG. 2 shows a schematic outline of the step-by-step synthesis of uniformly modified oligonucleotide thiophosphoramidates.

In other aspects, the invention is directed to a solid phase method of synthesizing oligonucleotide N3'→P5' thiophosphoramidates using a modification of the phosphoramidite transfer methodology of Nelson et al. (J. Organic Chemistry 62:7278–7287, 1997). The synthetic strategy employed 3'-NH-trityl-protected 3'-aminonucleoside 5'-O-cyanoethyl-N,N-10 diisopropylaminophosphoramidites (Nelson et al., cited above) that were purchased from Cruachem and JBL Scientific, Inc. (Aston, Pa. and San Luis Obispo, Calif., respectively). Every synthetic cycle (see FIG. 2) was conducted using the following chemical procedures: 1) detritylation, 2) coupling; 3) capping; 4) sulfurization. For a step-wise sulfurization of the internucleaside phosphoramidite group formed after the coupling step, the iodine/water based oxidizing agent was replaced by the sulfurizing agents—either by elemental sulfur $S_8$ or by the commonly used Beaucage reagent—3H-1,2-benzodithiol-3-one 1,1 dioxide (Iyer et al., J. Organic Chemistry, 55:4693–4699, 1990). The oligonucleotide syntheses were performed (1 $\mu$mole synthesis scale) with a 1% solution of Beaucage reagent in anhydrous acetonitrile or 15% $S_8$ in $CS_2/Et_3N$, 99/1 (vol/vol) as the sulfurizing agent.

Chimeric N3'→P5' phosphoramidate-phosphorthioamidate oligonucleotides can be made by using an oxidation step(s) after the coupling step, which results in formation of a phosphoramidate internucleoside group. Similarly, phosphodiester-phosphorthioamidates can be made by using 5'-phosphoramidite-3'-O-DMTr-protected nucleotides as monomeric building blocks. These synthetic approaches are known in the art.

The model phosphoramidate thymidine dinucleoside TnpsTn was prepared using both types of sulfurizing agents and has a 3'-NHP(O)(S⁻)O-5' internucleoside group. The reaction mixtures were analyzed and structure of the compound was confirmed by ion-exchange (IE) and reverse phase (RP) HPLC, and $^{31}P$ NMR. The analysis revealed that sulfurization of the internucleoside phosphoramidite group with Beaucage reagent resulted in formation of approximately 10–15% of the oxidized dinucleoside with 3'-NHP(O)(O⁻) O-5' phosphoramidate linkage ($^{31}P$ NMR δ, ppm 7.0 in $D_2O$). Alternatively, sulfurization with molecular sulfur $S_8$ produced the desired dinucleotide containing 3'-NHP(O) (S⁻)O-5' internucleoside group with practically quantitative yield, as was judged by $^{31}P$ NMR and IE HPLC analysis ($^{31}P$ NMR δ, ppm 56.4, 59.6 in $D_2O$, Rp,Sp isomers).

Similar results with regards to the sulfurization efficiency were obtained for the synthesis of model oligonucleotide 11-mer GTTAGGGTTAG (SEQ ID NO:1), where sulfurization with Beaucage reagent resulted in the full length product containing ~15% phosphoramidate linkages, as was judged by $^{31}P$ NMR analysis of the reaction mixture. Chemical shifts for the main peaks were ~57 and 60 ppm (broad doublets) and 7 ppm (broad singlet) corresponding to the thiophosphoramidate and phosphoramidate groups, respectively. In contrast, sulfurization with $S_8$ produced only ~2% phosphoramidate linkages in the 11-mer product according to the $^{31}P$ NMR analysis. The IE HPLC analysis of the oligomer was in good agreement with the $^{31}P$ NMR spectrum. Structure and purity of the final oligonucleotide products was confirmed by MALDI-TOF mass spectra analysis, by $^{31}P$ NMR, and by polyacrylamide gel electrophoretic analysis. The molecular mass for thiophosphoramidate oligomers $GT_2AG_3T_2AG$ (SEQ ID NO:1) and $TAG_3T_2AGACA_2$ (SEQ ID NO:2) was calculated to be 3,577.11 and 4,202.69, respectively. The molecular mass for thiophosphoramidate oligomers $GT_2AG_3T_2AG$ (SEQ ID NO:1) and $TAG_3T_2AGACA_2$ (SEQ ID NO:2) was determined experimentally by MALDI-TOF mass spectroscopy to be 3,577 and 4,203 respectively; mobility in 15% PAGE relative to isosequential phosphoramidates was 0.95 and 0.97 respectively.

Figure 3:
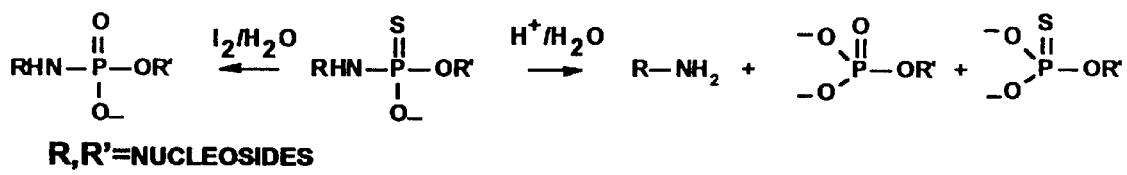
FIG. 3 shows a schematic outline of the conversion a dinucleotide thiophosphoramidate into its phosphoramidate counterpart, as well as the products resulting from the hydrolysis of the dinucleotide thiophosphoramidate.

The model phosphoramidate nucleoside TnpsTn was quantitatively converted into the phosphoramidate counterpart TnpTn, by treatment with 0.1 M iodine solution in pyridine/THF/$H_2O$ 1/4/0.1 (vol/vol), 55° C., 15 min, as judged by IE HPLC and $^{31}P$ NMR $^{31}P$ NMR δ ppm 7.0) (see FIG. 3). Treatment of the TnpsTn dinucleotide with 10% acetic acid, 55° C., 48 hr unexpectedly resulted in only partial hydrolysis (~10%) of internucleoside phosphoramidate linkage. For comparison under these conditions the parent phosphoramidate dimer TnpTn was completely hydrolyzed. Cleavage of the N—P bond in the dinucleotide thiophosphoramidate was accompanied by concomitant de-sulfurization process (~15%), followed by a rapid hydrolysis of the resultant phosphoramidate —NHP(O)(O⁻) O— group as revealed by IE HPLC and $^{31}P$ NMR (FIG. 3).

The 2'-$R_3$ N3'→P5' thiophosphoramidates can be obtained from the corresponding phosphoramidates as described above. The 2'-$R_3$ N3'→P5' phosphoramidates were obtained by the phosphoramidite transfer methodology devised for the synthesis of oligonucleotide N3'→P5' phosphoramidates. The synthesis of 2-O-alkyl N3'→P5' thiophosphoramidates is described in detail as an illustration of this methodology.

The appropriately protected 2'-O-alkyl-3' aminonucleoside-5'-phosphoramidite building blocks 4, 6, 11, and 15, where alkyl is methyl, were prepared according to a series of chemical transformations shown in Schemes 1–3 below. An inventive step for the preparation of these compounds was the selective methylation of the 2'-hybroxyl group in the presence of either the imino functionality of pyrimidines, or the N-7 atom of the purines. The two pyrimidine-based monomers were obtained from the known 3-azido-2'-O-acetyl-5'-O-toluoyl-3'-deoxy-β-D-ribofuranosyluracil 1. Typically, the N-3/O-4 imino nitrogen of 1 was first protected with a protecting group, such as by the reaction of methyl propyolate in the presence of dimethylaminopyridine (Scheme 1). The crude reaction product was then selectively 2'-O-deacetylated, and the resulting free 2'-hydroxyl group was then alkylated, such as by methylation using iodomethane and silver oxide. The N-3 protecting group was removed and the 3'-azido group was reduced to amine, which was then immediately protected, such as reaction with 4-monomethoxytritylchloride, to give the precursor 3. The 5'-toluoyl ester was then cleaved using an alkaline solution, followed by phosphitylation using known protocols to give the desired 2'-O-methyl uridine phosphoramidite monomer 4. The 2'-O-methyl cytosine phosphoramidite was obtained by conversion of uridine intermediate 3 into 3'-aminocytidine analogue 5.

Scheme 1

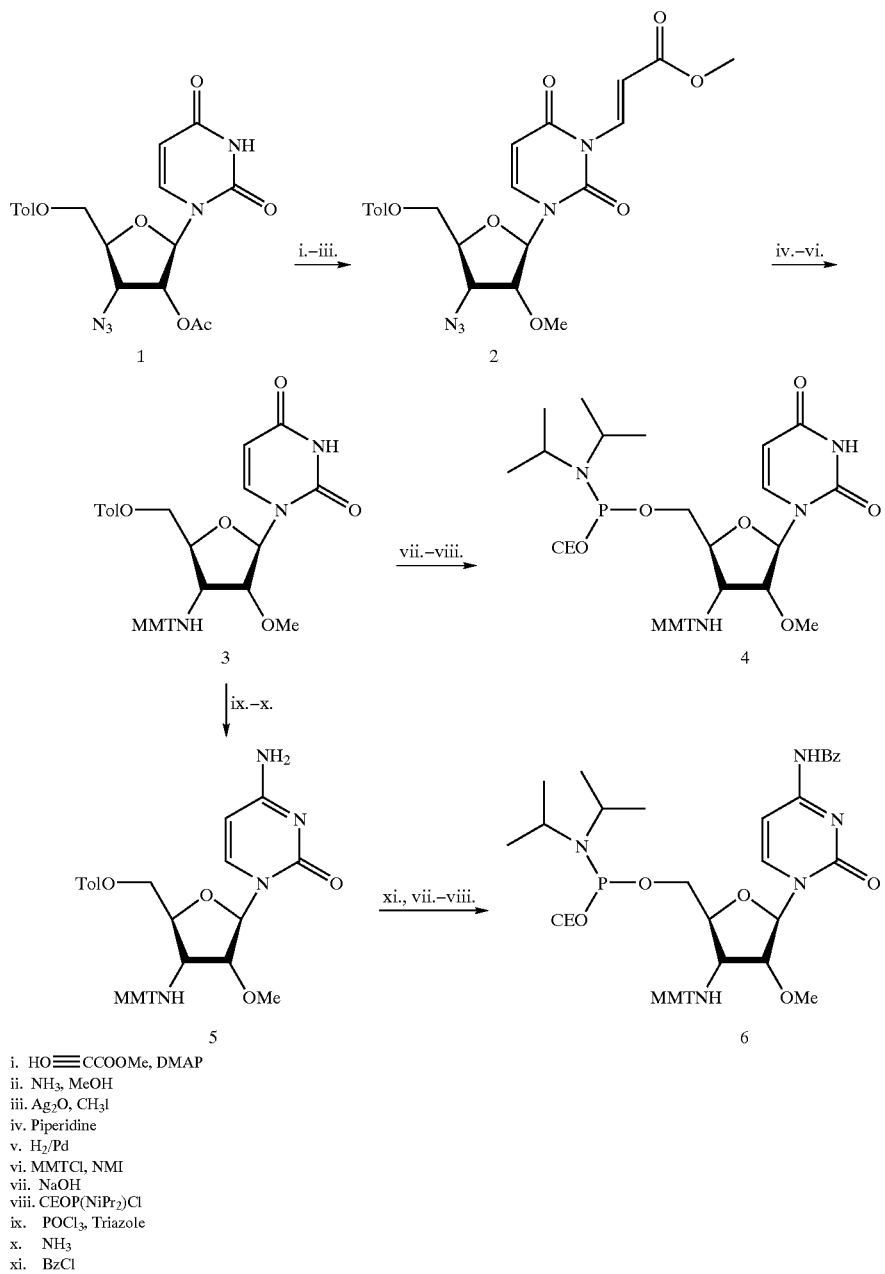

i. HO≡CCOOMe, DMAP
ii. NH₃, MeOH
iii. Ag₂O, CH₃I
iv. Piperidine
v. H₂/Pd
vi. MMTCl, NMI
vii. NaOH
viii. CEOP(NiPr₂)Cl
ix. POCl₃, Triazole
x. NH₃
xi. BzCl The synthesis of the 2'-O-alkyl adenosine analogue required the use of bulky protecting groups, primarily for exocyclic amine in order to prevent the alkylation of N-7 during methylation of the 2'-hydroxyl group (Scheme 2). 3'-Azido-2'-O-acetyl-5'-O-toluoyl-N⁶-benzoyl-3'-deoxyadenosine 7 was first deprotected, such as by reaction with NH₃/MeOH (1/1, v/v), to afford 3'-azido-3'-deoxyadenosine. Then, the 5'-hydrokyl group and the N-6 moiety were selectively re-protected with bulky protecting groups, such as the t-butyldiphenylsilyl group or the 4-monomethoxytrityl group. The combination of the two large substituents at the 5'-O and N-6 positions sterically occluded N-7, thereby allowing for the selective introduction of a methyl group at the 2'-position to produce the intermediate 8. The N-6 4-monomethoxytrityl group was then removed, such as by treatment with 3% trichloroacetic acid in an organic solvent, such as dichloromethane, followed by re-protection of N-6. The use of benzoyl chloride for the re-protection of N-6 resulted in the addition of two benzoyl groups. The second benzoyl group was subsequently removed by base treatment to produce the intermediate 9. The azide group was then reduced and the resulting 3'-amino group was protected with 4-monomethoxytrityl to form 10. Finally, the 5'-silyl protecting group was cleaved, and phosphitylation resulted in the 2'-O-methyl phosphoramidite monomer 11.

Scheme 2

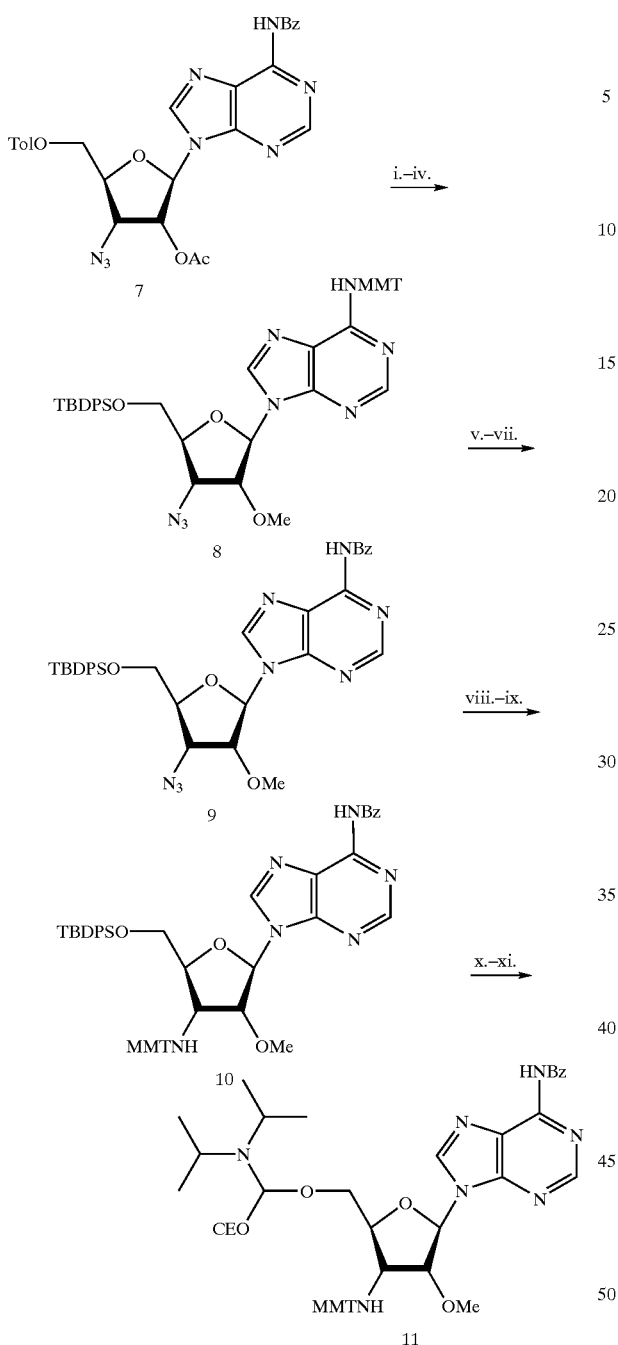

i. NH₃/MeOH
ii. TBDPSCl
iii. MMTCl, DMAP
iv. Ag₂O, MeI
v. TCA
vi. BzCl
vii. NaOH
viii. H₂/Pd
ix. MMTCl, NMI
x. TBAF
xi. CEOP(NiPr₂)Cl The synthesis of the guanosine-based 2'-O-alkyl phosphoramidite 15 is depicted in Scheme 3. 3'-Azido-2'-O-acetyl-5'-O-toluoyl-N²-isobutryl-O⁶-diphenylcarbamoyl-3'-10 deoxyguanosine 12 was deblocked by treatment with a base. The 5'O- and O-6 were reprotected by reaction with t-butyldiphenylsilylchloride. The bis-silylated intermediate was then 2'-O alkylated. The O-6 silyl group was selectively deprotected to give compound 13. The N-2 group was re-protected, the 3'-azido group was reduced, and the resulting 3'-amino group was protected to yield the nucleoside 14. Finally, the 2'-O-alkyl guanosine phosphoramidite monomer 15 was obtained by removing the 5'-protecting group followed by phosphitylation of the unmasked 5'-hydroxyl.

Scheme 3

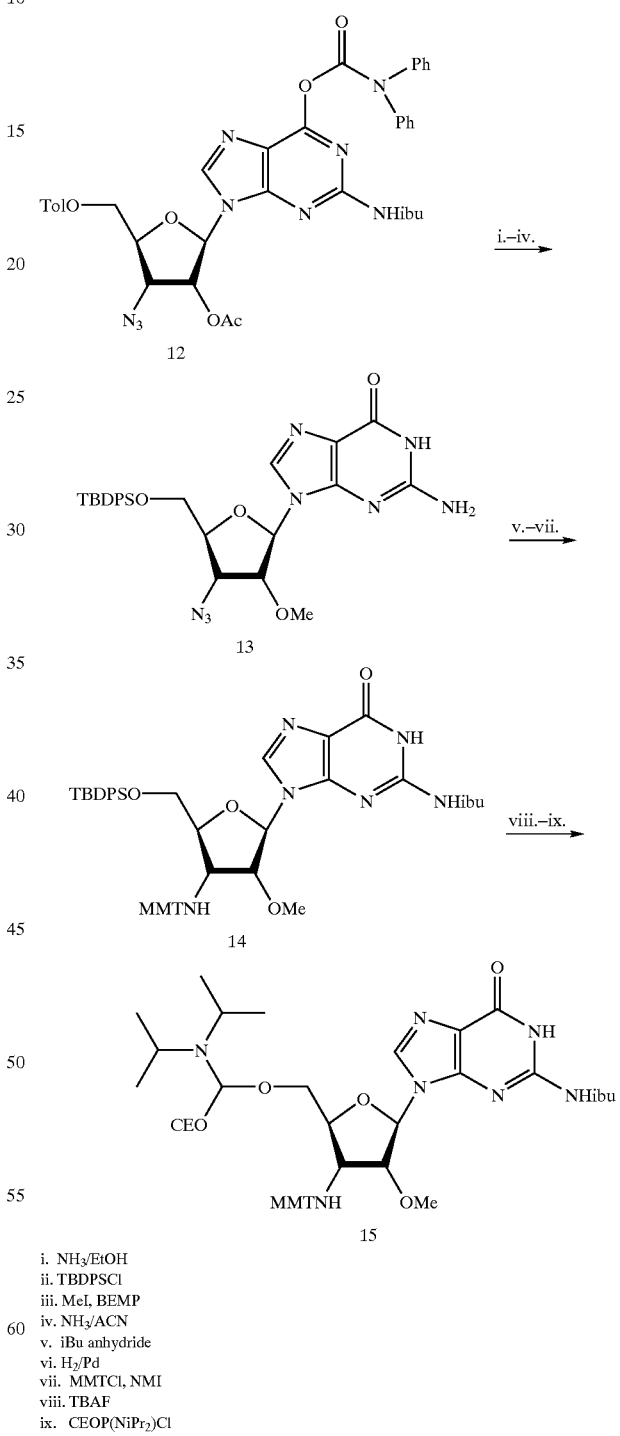

i. NH₃/EtOH
ii. TBDPSCl
iii. MeI, BEMP
iv. NH₃/ACN
v. iBu anhydride
vi. H₂/Pd
vii. MMTCl, NMI
viii. TBAF
ix. CEOP(NiPr₂)Cl In another embodiment of the present invention, the acid stability of oligonucleotides is increased by placing subunits linked by N3'→P5' thiophosphoramidate intersubunit linkages in the oligonucleotides. The hybridization properties of the thiophosphoramidate oligonucleotides were evaluated relative to complementary DNA or RNA strands having phosphodiester or phosphoramidate intersubunit linkages. The thermal stability data for duplexes generated from phosphoramidate oligonucleotides and phosphodiester oligomers are summarized in TABLE 1 (Example 3).

Hybridization of the thiophosphoramidate oligonucleotides with complementary nucleic acids is sequence specific and determined by the proper Watson-Crick base pairing. The duplex formed by phosphoramidate oligonucleotide SEQ ID NO:3 with a single base mismatch with a RNA target component of telomerase (Example 6, TABLE 2, Experiment 2) is substantially less stable than the duplex formed with oligonucleotide SEQ ID NO: 1 which is fully complementary to the RNA component of telomerase (Example 6, TABLE 2, Experiment 1).

Applications of Oligonucleotides Containing Internucleoside 3'-NHP (O) (S⁻) O-5' Thiophosphoramidate Linkages Oligonucleotide SEQ ID NO:2 3'-NHP(O)(S⁻)O-5' thiophosphoramidate was synthesized. This compound was surprisingly acid stable and formed a stable complex with a complementary RNA target. The N3'→P5' thiophosphoramidate polynucleotides of the present invention have great potential for anti-sense and anti-gene diagnostic/therapeutic applications. In a preferred embodiment of the present invention, the oligonucleotides are oligodeoxyribonucleotides.

A. Telomerase Inhibition Applications

Recently, an understanding of the mechanisms by which normal cells reach the state of senescence, i.e., the loss of proliferative capacity that cells normally undergo in the cellular aging process, has begun to emerge. The DNA at the ends, or telomeres, of the chromosomes of eukaryotes usually consists of tandemly repeated simple sequences. Scientists have long known that telomeres have an important biological role in maintaining chromosome structure and function. More recently, scientists have speculated that the cumulative loss of telomeric DNA over repeated cell divisions may act as a trigger of cellular senescence and aging, and that the regulation of telomerase, an enzyme involved in the maintenance of telomere length, may have important biological implications. See Harley, 1991, Mutation Research, 256:271–282. Experiments by Bodnar et al. have confirmed the importance of telomeres and telomerase in controlling the replicative lifespan of cultured normal human cells. See Bodnar et al., 1998, Science 279:349–352.

Telomerase is a ribonucleoprotein enzyme that synthesizes one strand of the telomeric DNA using as a template a sequence contained within the RNA component of the enzyme. See Blackburn, 1992, Annu. Rev. Biochem., 61:113–129. The RNA component of human telomerase has been sequenced and is 460 nucleotides in length containing a series of 11-base sequence repeats that is complementary to the telomere repeat. Human telomerase activity has been inhibited by a variety of oligonucleotides complementary to the RNA component of telomerase. See Norton et al., Nature Biotechnology, 14:615, 1996; Pitts et al., Proc. Natl. Acad. Sci., 95:11549–11554, 1998; and Glukhov et al., Bioch. Biophys. Res. Commun., 248:368–371, 1999. Thiophosphoramidate oligonucleotides of the present invention are complementary to 10 to 50 nucleotides of telomerase RNA. Preferably, the inventive telomerase inhibitor thiophosphoramidate oligonucleotides have a 10 to 20 consecutive base sequence that is complementary to telomerase RNA.

Methods for detecting telomerase activity, as well as for identifying compounds that regulate or affect telomerase activity, together with methods for therapy and diagnosis of cellular senescence and immortalization by controlling telomere length and telomerase activity, have also been described. See Feng et al., 1995, Science, 269:1236–1241; Kim et al., 1994, Science, 266:2011–2014; PCT patent publication No. 93/23572, published Nov. 25, 1993; and U.S. Pat. Nos. 5,656,638; 5,760,062; 5,767,278; 5,770,613 and 5,863,936.

The identification of compounds that inhibit telomerase activity provides important benefits to efforts at treating human disease. Compounds that inhibit telomerase activity can be used to treat telomerase-mediated disorders, such as cancer, since cancer cells express telomerase activity and normal human somatic cells do not possess telomerase activity at biologically relevant levels (i.e., at levels sufficient to maintain telomere length over many cell divisions). Unfortunately, few such compounds, especially compounds with high potency or activity and compounds that are bioavailable after oral administration, have been identified and characterized. Hence, there remains a need for compounds that act as telomerase inhibitors that have relatively high potency or activity and that are orally bioavailable, and for compositions and methods for treating cancer and other diseases in which telomerase activity is present abnormally.

The new thiophosphoramidate oligonucleotide compounds of the present invention are acid stable, and therefore, have many valuable uses as inhibitors of deleterious telomerase activity, such as, for example, in the treatment of cancer in humans. Pharmaceutical compositions of thiophosphoramidate oligonucleotide can be employed in treatment regimens in which cancer cells are inhibited, in vivo, or can be used to inhibit cancer cells ex vivo. Thus, this invention provides therapeutic compounds and compositions for treating cancer, and methods for treating cancer in mammals (e.g., cows, horses, sheep, steer, pigs and animals of veterinary interest such as cats and dogs). In addition, the phosphoramidate oligonucleotides of the present invention may also be used to treat other telomerase-mediated conditions or diseases, such as, for example, other hyperproliferative or autoimmune disorders.

As noted above, the immortalization of cells involves inter alia the activation of telomerase. More specifically, the connection between telomerase activity and the ability of many tumor cell lines to remain immortal has been demonstrated by analysis of telomerase activity (Kim et al., see above). This analysis, supplemented by data that indicates that the shortening of telomere length can provide the signal for replicative senescence in normal cells, see PCT application Ser. No. 93/23572, demonstrates that inhibition of telomerase activity can be an effective anti-cancer therapy. Thus, telomerase activity can prevent the onset of otherwise normal replicative senescence by preventing the normal reduction of telomere length and the concurrent cessation of cell replication that occurs in normal somatic cells after many cell divisions. In cancer cells, where the malignant phenotype is due to loss of cell cycle or growth controls or other genetic damage, an absence of telomerase activity permits the loss of telomeric DNA during cell division, resulting in chromosomal rearrangements and aberrations that lead ultimately to cell death. However, in cancer cells having telomerase activity, telomeric DNA is not lost during cell division, thereby allowing the cancer cells to become immortal, leading to a terminal prognosis for the patient. Agents capable of inhibiting telomerase activity in tumor cells offer therapeutic benefits with respect to a wide variety of cancers and other conditions (e.g., fungal infections) in which immortalized cells having telomerase activity are a factor in disease progression or in which inhibition of telomerase activity is desired for treatment purposes. The telomerase inhibitors of the invention can also be used to inhibit telomerase activity in germ line cells, which may be useful for contraceptive purposes.

In addition, it will be appreciated that therapeutic benefits for treatment of cancer can be realized by combining a telomerase inhibitor of the invention with other anti-cancer agents, including other inhibitors of telomerase such as described in U.S. Pat. Nos. 5,656,638; 5,760,062; 5,767,278; 5,770,613 and 5,863,936. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

The compounds of the present invention demonstrate inhibitory activity against telomerase activity in vivo, as can be demonstrated as described below. The in vitro activities of the compounds of the invention has also been demonstrated using the methods described herein. As used herein, the term "in vitro" refers to tests performed using living cells in tissue culture. Such procedures are also known as "ex vivo".

Oligonucleotide telomerase inhibitors described in this section typically comprise a sequence that is complementary to telomerase RNA component. The sequence of human telomerase RNA component is provided in U.S. Pat. No. 5,776,679. The telomerase RNA component of other species can also be used, depending on the intended subject of the therapy.

Generally, the oligonucleotide will comprise between about 10 and 100 nucleotides that are specific for telomerase (that is, they hybridize with telomerase RNA component at lower concentrations or under conditions of greater stringency than they will with other RNA enzyme components, or other RNA molecules expected to be present and functionally active in the target cells or therapeutic bystander cells). Included are oligonucleotides between about 10 and 25 nucleotides, exemplified by oligonucleotides between 12 and 15 nucleotides, illustrated in the Examples below. In many circumstances, the oligonucleotide will be exactly complementary to a consecutive sequence of the same length in telomerase RNA. Nevertheless, it is understood that hybridization can still be specific even when there are mismatched residues or gaps or additions in the oligonucleotide, especially when the length of the corresponding complementary sequence in the RNA is longer than 15 nucleotides.

One method used to identify thiophosphoramidate polynucleotides of the invention with specific sequences that inhibit telomerase activity involves placing cells, tissues, or preferably a cellular extract or other preparation containing telomerase in contact with several known concentrations of a thiophosphoramidate oligonucleotide that is complementary to the RNA component of telomerase in a buffer compatible with telomerase activity. The level of telomerase activity for each concentration of the thiophosphoramidate polynucleotide is measured. Before and after administration of a telomerase inhibitor, telomerase activity can be determined using standard reagents and methods. For example, telomerase acvitity in cultured cells can be measured using TRAP activity assay (Kim et al., Science 266:2011, 1997; Weinrich et al., Nature Genetics 17:498, 1997). The following assay kits are available commercially for research purposes: TRAPeze® XK Telomerase Detection Kit (Cat. s7707, Intergen Co., Purchase N.Y.); and TeloTAGGG Telomerase PCR ELISAplus (Cat. 2,013,89, Roche Diagnostics, Indianapolis Ind.).

The $IC_{50}$ (the concentration of the polynucleotide at which the observed activity for a sample preparation is observed to fall one-half of its original or a control value) for the polynucleotide is determined using standard techniques. Other methods for determining the inhibitory concentration of a compound of the invention against telomerase can be employed as will be apparent to those of skill in the art based on the disclosure herein.

With the above-described methods, $IC_{50}$ values for several of the thiophosphoramidate oligonucleotides of the present invention were determined, and found to be below 10 nM (see TABLE 2, Example 6).

With respect to the treatment of malignant diseases using thiophosphoramidate polynucleotides that are complementary to the RNA component of telomerase are expected to induce crisis in telomerase-positive cell lines. Treatment of HME50-5E human breast epithelial cells that were spontaneously immortalized with thiophosphoramidate oligonucleotide SEQ ID NO:2 resulted in inhibition of telomerase activity as demonstrated by the decrease in telomere length (see Example 6, and FIG. 4). Treatment of other telomerase-positive cell lines, such as HEK-293 and HeLa cells, with inventive thiophosphoramidate oligonucleotides that are complementary to the RNA sequence component of telomerase is also expected to induce a reduction of telomere length in the treated cells.

Thiophosphoramidate oligonucleotides of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., a thiophosphoramidate oligonucleotide that has at least one single base mismatch with the complementary telomerase RNA target. The thiophosphoramidate oligonucleotides of the invention also are expected to demonstrate no significant cytotoxic effects at concentrations below about 20 μM in the normal cells.

In addition, the specificity of the thiophosphoramidate oligonucleotides of the present invention for telomerase RNA can be determined by performing hybridization tests with and comparing their activity ($IC_{50}$) with respect to telomerase and to other enzymes known to have essential RNA components, such as ribonucleoase P. Compounds having lower $IC_{50}$ values for telomerase as compared to the $IC_{50}$ values toward the other enzymes being screened are said to possess specificity for telomerase.

In vivo testing can also be performed using a mouse xenograft model, for example, in which OVCAR-5 tumor cells are grafted onto nude mice, in which mice treated with a thiophosphoramidate oligonucleotide of the invention are expected to have tumor masses that, on average, may increase for a period following the initial dosing, but will begin to shrink in mass with continuing treatment. In contrast, mice treated with a control (e.g., a thiophosphoramidate oligonucleotide that has at least one single base mismatch with the complementary telomerase RNA target) are expected to have tumor masses that continue to increase.

From the foregoing those skilled in the art will appreciate that the present invention also provides methods for selecting treatment regimens involving administration of a thiophosphoramidate oligonucleotide of the invention. For such purposes, it may be helpful to perform a terminal restriction fragment (TRF) analysis in which DNA from tumor cells is analyzed by digestion with restriction enzymes specific for sequences other than the telomeric $(T_2AG_3)N$ sequence. Following digestion of the DNA, gel electrophoresis is performed to separate the restriction fragments according to size. The separated fragments are then probed with nucleic acid probes specific for telomeric sequences to determine the lengths of the terminal fragments containing the telomere DNA of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

Thus, in one aspect, the present invention provides compounds that can serve in the war against cancer as important weapons against malignancies expressing telomerase, tumors including skin, connective tissue, adipose, breast, lung, stomach, pancreas, ovary, cervix, uterus, kidney, bladder, colon, prostate, central nervous system (CNS), retina and circulating tumors (such as leukemia and lymphoma). In particular, the thiophosphoramidate polynucleotides of the present invention can provide a highly general method of treating many, if not most, malignancies, as demonstrated by the highly varied human tumor cell lines and tumors having telomerase activity. More importantly, the thiophosphoramidate oligonucleotides of the present invention can be effective in providing treatments that discriminate between malignant and normal cells to a high degree, avoiding many of the deleterious side-effects present with most current chemotherapeutic regimes which rely on agents that kill dividing cells indiscriminately.

B. Other Antisense Applications

Antisense therapy involves the administration of exogenous oligonucleotides that bind to a target nucleic acid, typically an RNA molecule, located within cells. The term antisense is so given because the oligonucleotides are typically complementary to mRNA molecules ("sense strands") which encode a cellular product.

The thiophosphoramidate oligonucleotides described herein are useful for antisense inhibition of gene expression (Matsukura et al., Proc. Natl. Acad. Sci., 86:4244–4248, 1989; Agrawal et al., Proc. Natl. Acad. Sci., 86:7790–7794, 1989; Zamecnik et al., Proc. Natl. Acad. Sci., 83:4143–4146, 1986; Rittner and Sczakiel, Nucleic Acids Research, 19:1421–1426, 1991; Stein and Cheng, Science, 261:1004–1012, 1993). Oligonucleotides containing N3'→P5' thiophosphoramidate linkages have therapeutic applications for a large number of medically significant targets, including, but not limited to inhibition of cancer cell proliferation and interference with infectious viruses. The N3'→P5' thiophosphoramidate oligonucleotides are useful for both veterinary and human applications. The high acid stability of the inventive oligonucleotides and their ability to act effectively as antisense molecules at low concentrations (see below) make these oligonucleotides highly desirable as therapeutic antisense agents.

Anti-sense agents typically need to continuously bind all target RNA molecules so as to inactivate them or alternatively provide a substrate for endogenous ribonuclease H (Rnase H) activity. Sensitivity of RNA/oligonucleotide complexes, generated by the methods of the present invention, to Rnase H digestion can be evaluated by standard methods (Donia et al., J. Biol. Chem., 268:14514–14522, 1993; Kawasaki et al., J. Medicinal Chem., 36:831–841, 1993).

The compounds and methods of the present invention provide several advantages over the more conventional antisense agents. First, thiophosphoramidate oligonucleotides bind more strongly to RNA targets as corresponding phosphodiester oligonucleotides. Second, the thiophosphoramidate oligonucleotides are more resistant to degradation by acid conditions. Third, in cellular uptake of the compound, an uncharged thiophosphoramidate polynucleotide backbone may allow more efficient entry of the phosphoramidate oligonucleotides into cells than a charged oligonucleotide.

Further, when an RNA is coded by a mostly purine strand of a duplex target sequence, phosphoramidate analog oligonucleotides targeted to the duplex also have potential for inactivating the DNA—i.e., the ability to inactivate a pathogen in both single-stranded and double-stranded forms (see discussion of anti-gene therapies below).

Sequence-specific thiophosphoramidate oligonucleotide molecules are potentially powerful therapeutics for essentially any disease or condition that in some way involves RNA. Exemplary modes by which such sequences can be targeted for therapeutic applications include:

a) targeting RNA sequences expressing products involved in the propagation and/or maintenance infectious agents, such as, bacteria, viruses, yeast and other fungi, for example, a specific mRNA encoded by an infectious agent;

b) formation of a duplex molecule that results in inducing the cleavage of the RNA (e.g., Rnase H cleavage of RNA/DNA hybrid duplex molecules);

c) blocking the interaction of a protein with an RNA sequence (e.g., the interaction of TAT and TAR, see below); and d) targeting sequences causing inappropriate expression or proliferation of cellular genes: for example, genes associated with cell cycle regulation; inflammatory processes; smooth muscle cell (SMC) proliferation, migration and matrix formation (Liu et al., Circulation, 79:1374–1387, 1989); certain genetic disorders; and cancers (protooncogenes).

In one embodiment, translation or RNA processing of inappropriately expressed cellular genes is blocked. Exemplary potential target sequences are protooncogenes, for example, including but not limited to the following: c-myc, c-myb, c-fos, c-kit, ras, and BCR/ABL (e.g., Wickstrom, Editor, Prospects for Antisense Nucleic Acid Therapy of Cancer and AIDS, Wiley-Liss, New York, N.Y., 1991; Zalewski et al., Circulation Res., 88:1190–1195, 1993; Calabretta et al., Seminars in Cancer Biol., 3:391–398, 1992; Calabretta et al., Cancer Treatment Rev. 19:169–179, 1993), oncogenes (e.g., p53, Bayever et al. Antisense Research and Development, 3:383–390, 1993), transcription factors (e.g., NF.kappa.B, Cogswell et al., J. Immunol., 150:2794–2804, 1993) and viral genes (e.g., papillomaviruses, Cowsert et al., Antimicrob. Agents and Chemo., 37:171–177, 1993; herpes simplex virus, Kulka et al., Antiviral Res., 20:115–130, 1993). Another suitable target for antisense therapy in hyperplasias is the protein component of telomerase (see WO 99/50279), which is often the limiting component in telomerase expression. The sequence of human telomerase reverse transcriptase is provided in issued U.S. Pat. No. 6,093,809, in WO 98/14592, and in pGRN121 (ATCC Accession No. 209016). To further illustrate, two RNA regions of the HIV-1 protein that can be targeted by the methods of the present invention are the REV-protein response element (RRE) and the TAT-protein transactivation response element (TAR). REV activity requires the presence of the REV response element (RRE), located in the HIV envelope gene (Malim et al., Nature, 338:254–257, 1989; Malim et al., Cell, 58:205–214, 1989).

The RRE has been mapped to a 234-nucleotide region thought to form four stem-loop structures and one branched stem-loop structure (Malim et al., Nature, 338:254–257, 1989). Data obtained from footprinting studies (Holland et al., J. Virol., 64:5966–5975, 1990; Kjems et al., Proc. Natl. Acad. Sci., 88:683–687, 1991) suggest that REV binds to six base pairs in one stem structure and to three nucleotides in an adjacent stem-loop structure of the RRE. A minimum REV binding region of about 40 nucleotides in stem-loop II has been identified by Cook, et al. (Nucleic Acids Research, 19:1577–1583). This binding region can be target for generation of RNA/DNA duplexes (e.g., Li et al., J. Virol., 67:6882–6888, 1993) using one or more thiophosphoramidate oligonucleotides, according to the methods of the present invention.

The HIV-1 TAT is essential for viral replication and is a potent transactivator of long terminal repeat (LTR)-directed viral gene expression (Dayton et al., Cell, 44:941–947, 1986; Fisher et al., Nature, 320:367–371, 1986). Transactivation induced by TAT protein requires the presence of the TAR element (See U.S. Pat. No. 5,837,835) which is located in the untranslated 5' end of the viral mRNA element.

The TAR element is capable of forming a stable stem-loop structure (Muesing et al., Cell, 48:691–701, 1987). The integrity of the stem and a 3 nucleotide (nt) bulge on the stem of TAR has been demonstrated to be essential for specific and high-affinity binding of the TAT protein to the TAR element (Roy et al., Genes Dev., 4:1365–1373, 1990; Cordingley et al., Proc. Natl. Acad. Sci., 87:8985–8989, 1990; Dingwall et al., Proc. Natl. Acad. Sci., 86:6925–6929, 1989; Weeks et al., Science, 249:1281–1285, 1990). This region can be targeted for anti-sense therapy following the method of the present invention.

In addition to targeting the RNA binding sites of the REV, RRE and TAT proteins, the RNA coding sequences for the REV and TAT proteins themselves can be targeted in order to block expression of the proteins.

Initial screening of N3'→P5' thiophosphoramidate oligonucleotides, directed to bind potential antisense target sites, typically includes testing for the thermal stability of resultant RNA/DNA duplexes. When a thiophosphoramidate oligonucleotide is identified that binds a selected RNA target sequence, the oligonucleotide is further tested for inhibition of RNA function in vitro. Cell culture assays systems are used for such in vitro analysis (e.g., herpes simplex virus, Kulka et al., Antiviral Res., 20:115–130, 1993; HIV-1, Li et al., J. Virol., 67:6882–6888, 1993, Vickers et al., Nucleic Acids Research, 19:3359–3368, 1991; coronary smooth muscle cell proliferation in restenosis, Zalewski et al., Nucleic Acids Research, 15:1699–1715, 1987; IL-2R, Grigoriev et al., Proc. Natl. Acad. Sci., 90:3501–3505, 1993; c-myb, Baer et al., Blood, 79:1319–1326, 1992; c-fos, Cutry et al., J. Biol. Chem., 264:19700–19705, 1989; BCR/ABL, Szczylik et al., Science, 253:562–565, 1991).

C. Anti-gene Applications

Inhibition of gene expression via triplex formation has been previously demonstrated (Cooney et al., Science, 241:456–459, 1989; Orson et al., Nucleic Acids Research, 19:3435–3441, 1991; Postel et al., Proc. Natl. Acad. Sci., 88:8227–8231, 1991). The increased stability of triplex structures formed when employing third strand thiophosphoramidate analog oligonucleotides provides a stronger tool for antigene applications, including veterinary and human therapeutic applications.

A target region of choice is selected based on known sequences using standard rules for triplex formation (Helene and Toulme, Biochem. Biophys. Acta, 1049:99–125, 1990). Typically, the thiophosphoramidate oligonucleotide sequence is targeted against double-stranded genetic sequences in which one strand contains predominantly purines and the other strand contains predominantly pyrimidines.

Thiophosphoramidate oligonucleotides of the present invention are tested for triplex formation against a selected duplex target sequences using band shift assays (see for example, U.S. Pat. No. 5,726,297, Example 4). Typically, high percentage polyacrylamide gels are used for band-shift analysis and the levels of denaturing conditions (Ausubel et al., Current Protocols in Molecular Biology, Hohn Wiley and Sons, Inc. Media Pa.; Sauer et al. Editor, Methods in Enzymology Protein/DNA Interactions, Academic Press, 1991; Sambrook et al., In Molecular Cloning: A Laboratory Manual, Cold Spring Harbor Press, Vol. 2, 1989) are adjusted to reduce any non-specific background binding.

The duplex target is labeled (for example, using a radioactive nucleotide) and mixed with a third strand oligonucleotide, being tested for its ability to form triplex structures with the target duplex. A shift of the mobility of the labeled duplex oligonucleotide indicates the ability of the oligonucleotide to form triplex structures.

Triplex formation is indicated in the band shift assay by a decreased mobility in the gel of the labeled triplex structure relative to the labeled duplex structure.

Numerous potential target sites can be evaluated by this method including target sites selected from a full range of DNA sequences that vary in length as well as complexity. Sequence-specific thiophosphoramidate analog binding molecules are potentially powerful therapeutics for essentially any disease or condition that in some way involves DNA. Exemplary target sequences for such therapeutics include: a) DNA sequences involved in the propagation and/or maintenance of infectious agents, such as, bacterial, viruses, yeast and other fungi, for example, disrupting the metabolism of an infectious agent; and b) sequences causing inappropriate expression or proliferation of cellular genes, such as oncogenes, for example, blocking or reducing the transcription of inappropriately expressed cellular genes (such as genes associated with certain genetic disorders).

Gene expression or replication can be blocked by generating triplex structures in regions to which required regulatory proteins (or molecules) are known to bind (for example, HIV transcription associated factors like promoter initiation sites and SP1 binding sites, McShan et al., J. Biol. Chem., 267:5712–5721, 1992). Alternatively, specific sequences within protein-coding regions of genes (e.g., oncogenes) can be targeted as well.

When a thiophosphoramidate analog oligonucleotide is identified that binds a selected duplex target sequence tests, for example, by the gel band shift mobility assay described above, the analog is further tested for its ability to form stable triplex structures in vitro. Cell culture and in vivo assay systems, such as those described U.S. Pat. No. 5,631,135, are used.

Target sites can be chosen in the control region of the genes, e.g., in the transcription initiation site or binding regions of regulatory proteins (Helene and Toulme, 1990; Birg et al., 1990; Postel et al., 1991; Cooney et al., 1988). Also, target sites can be chosen such that the target also exists in mRNA sequences (i.e., a transcribed sequence), allowing oligonucleotides directed against the site to function as antisense mediators as well (see above).

Also, thiophosphoramidate modified DNA molecules can be used to generate triplex molecules with a third strand target (i.e., a single-strand nucleic acid). For example, a DNA molecule having two regions capable of forming a triplex structure with a selected target third strand molecule can be synthesized. Typically the two regions are linked by a flexible region which allows the association of the two regions with the third strand to form a triplex.

Hinge regions can comprise any flexible linkage that keeps the two triplex forming regions together and allows them to associate with the third strand to form the triplex. Third strand targets are selected to have appropriate purine|pyrimidine content so as to allow formation of triplex molecules.

The flexible linkage may connect the two triplex forming regions (typically, complementary DNA strands) in any selected orientation depending on the nature of the base sequence of the target. For example, the two triplex forming regions each have 5' and 3' ends, these ends can be connected by the flexible hinge region in the following orientations: 5' to 3', 3' to 5', 3' to 3', and 5' to 5'.

Further, duplex DNA molecules containing at least one thiophosphoramidate linkage in each strand can be used as decoy molecules for transcription factors or DNA binding proteins (e.g., c-myb).

Single-stranded DNA can also be used as a target nucleic acid for oligonucleotides of the present invention, using, for example, thiophosphoramidate intersubunit linkage-containing hairpin structures. Two thiophosphoramidate analog oligonucleotides can be selected for single-strand DNA target-directed binding. Binding of the two phosphoramidate analog strands to the single-strand DNA target results in formation of a triplex.

D. Pharmaceutical Compositions

The present invention includes pharmaceutical compositions useful in antisense and antigene therapies. The compositions comprise an effective amount of N3'→P5' thiophosphoramidate oligonucleotides in combination with a pharmaceutically acceptable carrier. One or more N3'→P5' thiophosphoramidate oligonucleotides (having different base sequences or linkages) may be included in any given formulation.

The N3'→P5' thiophosphoramidate oligonucleotides, when employed in therapeutic applications, can be formulated neat or with the addition of a pharmaceutical carrier. The pharmaceutical carrier may be solid or liquid. The formulation is then administered in a therapeutically effective dose to a subject in need thereof.

Liquid carriers can be used in the preparation of solutions, emulsions, suspensions and pressurized compositions. The N3'→P5' thiophosphoramidate oligonucleotides are dissolved or suspended in a pharmaceutically acceptable liquid excipient. Suitable examples of liquid carriers for parenteral administration of N3'→P5' thiophosphoramidate oligonucleotides preparations include water (partially containing additives, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of N3'→P5' thiophosphoramidate oligonucleotides the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. For example, antisense oligonucleotides directed against retinal cytomegalovirus infection may be administered topically by eyedrops. N3'→P5' thiophosphoramidate oligonucleotides can also be administered intravascularly or via a vascular stent impregnated with mycophenolic acid, for example, during balloon catheterization to provide localized anti-restenosis effects immediately following injury.

The liquid carrier for pressurized compositions can be halogenated hydrocarbon or other pharmaceutically acceptable propellant. Such pressurized compositions may also be lipid encapsulated for delivery via inhalation. For administration by intranasal or intrabronchial inhalation or insufflation, N3'→P5' thiophosphoramidate oligonucleotides may be formulated into an aqueous or partially aqueous solution, which can then be utilized in the form of an aerosol, for example, for treatment of infections of the lungs like *Pneumocystis carnii*.

N3'→P5' thiophosphoramidate oligonucleotides may be administered topically as a solution, cream, or lotion, by formulation with pharmaceutically acceptable vehicles containing the active compound. For example, for the treatment of genital warts.

The N3'→P5' thiophosphoramidate oligonucleotides may be administered in liposome carriers. The use of liposomes to facilitate cellular uptake is described, for example, in U.S. Pat. No. 4,897,355 and U.S. Pat. No. 4,394,448. Numerous publications describe the formulation and preparation of liposomes.

The dosage requirements for treatment with N3'→P5' thiophosphoramidate oligonucleotides vary with the particular compositions employed, the route of administration, the severity of the symptoms presented, the form of N3'→P5' thiophosphoramidate oligonucleotides and the particular subject being treated.

For use as an active ingredient in a pharmaceutical preparation, an oligonucleotide of this invention is generally purified away from other reactive or potentially immunogenic components present in the mixture in which they are prepared. Typically, each active ingredient is provided in at least about 90% homogeneity, and more preferably 95% or 99% homogeneity, as determined by functional assay, chromatography, or gel electrophoresis. The active ingredient is then compounded into a medicament in accordance with generally accepted procedures for the preparation of pharmaceutical preparations.

Pharmaceutical compositions of the invention can be administered to a subject in a formulation and in an amount effective to achieve any clinically desirable result. For the treatment of cancer, desirable results include reduction in tumor mass (as determined by palpation or imaging; e.g., by radiography, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor-specific markers such as serum PSA), and improvement in quality of life (as determined by clinical assessment, e.g., Karnofsky score). For the treatment of viral infection, desirable results include reduction or elimination of the infection, the formation of infectious particles, or resolution of disease-associated symptoms.

The amount of oligonucleotide per dose and the number of doses required to achieve such effects can be determined empirically using in vitro tests and animal models (illustrated in Example 9). An appropriate range for testing can be estimated from the 50% inhibitory concentration determined with isolated telomerase or cultured cells. Preparations of isolated telomerase can be obtained according to U.S. Pat. No. 5,968,506. Typically, the formulation and route of administration will provide a local concentration at the disease site of between 1 $\mu$M and 1 nM for a stable oligonucleotide of 12–15 nucleosides that is 100% identical to an enzyme-specific target RNA sequence. The ultimate responsibility for determining the administration protocol is in the hands of the managing clinician.

In general, N3'→P5' thiophosphoramidate oligonucleotides are administered at a concentration that affords effective results without causing any harmful or deleterious side effects (e.g., an effective amount). Such a concentration can be achieved by administration of either a single unit dose, or by the administration of the dose divided into convenient subunits at suitable intervals throughout the day.

E. Diagnostic Applications

The thiophosphoramidate oligonucleotides of the present invention are also useful in diagnostic assays for detection of RNA or DNA having a given target sequence. In one general application, the thiophosphoramidate oligonucleotides are labeled (e.g., isotopically or other detectable reporter group) and used as probes for DNA or RNA samples that are bound to a solid support (e.g., nylon membranes).

Alternatively, the thiophosphoramidate oligonucleotides may be bound to a solid support (for example, magnetic beads) and homologous RNA or DNA molecules in a sample separated from other components of the sample based on their hybridization to the immobilized phosphoramidate analogs. Binding of thiophosphoramidate oligonucleotides to a solid support can be carried out by conventional methods. Presence of the bound RNA or DNA can be detected by standard methods, for example, using a second labeled reporter or polymerase chain reaction (See U.S. Pat. Nos. 4,683,195 and 4,683,202).

Diagnostic assays can be carried out according to standard procedures, with suitable adjustment of the hybridization conditions to allow thiophosphoramidate oligonucleotide hybridization to the target region. The ability of thiophosphoramidate oligonucleotides to bind at elevated temperature can also help minimize competition for binding to a target sequence between the thiophosphoramidate oligonucleotides probe and any corresponding single-strand phosphodiester oligonucleotide that is present in the diagnostic sample.

Thiophosphoramidate oligonucleotides designed for use in hybridization assays and other protocols described in this disclosure can be packaged in kit form. The oligonucleotide is provided in a container, typically in a buffer suitable for long-term storage, and is optionally accompanied by other reagents, standards, or controls useful in conducting the reaction. Typically, the kit will also be accompanied by written indications for use of the oligonucleotide in a hybridization reaction or diagnostic assay, either as a product insert or by associated literature in distribution or marketing of the kit.

F. Other Applications

In one aspect, the thiophosphoramidate oligonucleotides can be used in methods to enhance isolation of RNA or DNA from samples. For example, as discussed above, thiophosphoramidate oligonucleotides can be fixed to a solid support and used to isolate complementary nucleic acid sequences, for example, purification of a specific mRNA from a polyA fraction (Goldberg et al., Methods in Enzmology, 68:206, 1979). The thiophosphoramidate oligonucleotides are advantageous for such applications since they can form more stable interactions with RNA and duplex DNA than standard phosphodiester oligonucleotides.

A large number of applications in molecular biology can be found for reporter labeled thiophosphoramidate oligonucleotides, particularly for the detection of RNA in samples. Thiophosphoramidate oligonucleotides can be labeled with radioactive reporters ($^3$H, $^{14}$C, $^{32}$P, or $^{35}$S nucleosides), biotin or fluorescent labels (Gryaznov et al., Nucleic Acids Research, 20:3403–3409, 1992). Labeled thiophosphoramidate oligonucleotides can be used as efficient probes in, for example, RNA hybridization reactions (Ausubel et al., Current Protocols in Molecular Biology, Hohn Wiley and Sons, Inc., Media, Pa.; Sambrook et al., In Molecular Cloning: A Laboratory Manual, Cold Spring Harbor Laboratory Press, Vol. 2, 1989).

Also, double-stranded DNA molecules where each strand contains at least one thiophosphoramidate linkage can be used for the isolation of DNA-duplex binding proteins. In this embodiment the duplex containing thiophosphoramidate intersubunit linkages is typically affixed to a solid support and sample containing a suspected binding protein is then passed over the support under buffer conditions that facilitate the binding of the protein to its DNA target. The protein is typically eluted from the column by changing buffer conditions.

The triplex forming DNA molecules described above, containing thiophosphoramidate modified linkages, can be used as diagnostic reagents as well, to, for example, detect the presence of a DNA molecule in a sample.

Further, complexes containing oligonucleotides having N3'→P5' thiophosphoramidate intersubunit linkages can be used to screen for useful small molecules or binding proteins: for example, N3'→P5' thiophosphoramidate oligonucleotide complexes with duplex DNA can be used to screen for small molecules capable of further stabilizing the triplex structure. Similar screens are useful with N3'→P5' thiophosphoramidate oligonucleotide complexes formed with single strand DNA and RNA molecules.

G. Variations

Variations on the thiophosphoramidate oligonucleotides used in the methods of the present invention include modifications to facilitate uptake of the oligonucleotide by the cell (e.g., the addition of a cholesterol moiety (Letsinger, U.S. Pat. No. 4,958,013); production of chimeric oligonucleotides using other intersubunit linkages (Goodchild, Bioconjugate Chem., 1:165–187, 1990); modification with intercalating agents (for example, triplex stabilizing intercalating agents, Wilson et al., Biochemistry, 32:10614–10621, 1993); and use of ribose instead of deoxyribose subunits.

Further modifications include, 5' and 3' terminal modifications to the oligonucleotides (e.g., —OH, —OR, —NHR, —NH$_2$ and cholesterol). In addition, the ribose 2' position can be the site of numerous modifications, including, but not limited to, halogenation (e.g., —F).

N3'→P5' thiophosphoramidate oligonucleotides may also be modified by conjugation to a polypeptide that is taken up by specific cells. Such useful polypeptides include peptide hormones, antigens and antibodies. For example, a polypeptide can be selected that is specifically taken up by a neoplastic cell, resulting in specific delivery of N3'→P5' thiophosphoramidate oligonucleotides to that cell type. The polypeptide and oligonucleotide can be coupled by means known in the art (see, for example, PCT International Application Publication No. PCT/US89/02363, WO 89/12110, published Dec. 14, 1989, Ramachandr, K. et al.).

The properties of such modified thiophosphoramidate oligonucleotides, when applied to the methods of the present invention, can be determined by the methods described herein.

EXAMPLE 1

General Methods $^{31}$P NMR spectra were obtained on a Varian 400 Mhz spectrometer. $^{31}$P NMR spectra were referenced against 85% aqueous phosphoric acid. Anion exchange HPLC was performed using a Dionex DX 500 Chromatography System, with a Pharmacia Bitotech Mono Q HR 5/5 or 10/16 ion exchange columns. Mass spectral analysis was performed by Mass Consortium, San Diego, Calif. MALDI-TOF analysis of oligonucleotides was obtained using a PerSpective Biosystems Voyager Elite mass spectrometer with delayed extraction. Thermal dissociation experiments were conducted on a Cary Bio 100 UV-Vis spectrometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic anhydride, 1,2-dichloroethane, and dioxane were purchased from Aldrich (Milwaukee, Wis.).

All non-thiophosphoramidate oligonucleotides were synthesized on an ABI 392 or 394 DNA synthesizer using standard protocols for the phosphoramidite based coupling approach (Caruthers, Acc. Chem. Res., 24:278–284, 1991). The chain assembly cycle for the synthesis of oligonucleotide phosphoramidates was the following: (i) detritylation, 3% trichloroaceticacid in dichloromethane, 1 min; (ii) coupling, 0.1 M phosphoramidite and 0.45 M tetrazole in acetonitrile, 10 min; (iii) capping, 0.5 M isobutyic anhydride in THF/lutidine, 1/1, v/v, 15 sec; and (iv) oxidation, 0.1 M iodine in THF/pyridine/water, 10/10/1, v/v/v, 30 sec.

Chemical steps within the cycle were followed by acetonitrile washing and flushing with dry argon for 0.2–0.4 min. Cleavage from the support and removal of base and phosphoramidate protecting groups was achieved by treatment with ammonia/EtOH, 3/1, v/v, for 6 h at 55° C. The oligonucleotides were concentrated to dryness in vacuo after which the 2'-t-butyldimethylsilyl groups were removed by treatment with 1M TBAF in THF for 4–16 h at 25° C. The reaction mixtures were diluted with water and filtered through a 0.45 nylon acrodisc (from Gelman Sciences, Ann Arbor, Mich.). Oligonucleotides were then analyzed and purified by IE HPLC and finally desalted using gel filtration on a Pharmacia NAP-5 or NAP-25 column. Gradient conditions for IE HPLC: solvent A (10 mM NaOH), solvent B (10 mM NaOH and 1.5 M NaCl); solvent A for 3 min then a linear gradient 0–80% solvent B within 50 min.

EXAMPLE 2

Synthesis of Arabino-fluorooligonucleotide N3'→P5' Phosphoramidates

The solid phase synthesis of oligo-2'-arabino-fluoronucleotide N3'→P5' phosphoramidates was based on the phosphoramidite transfer reaction employing the monomer building blocks—5'-(O-cyanoethyl-N,N'-diisopropylamino)-phosphoramidites of 3'-MMTr-protected-3'-amino-2'-ara-fluoro nucleosides. Preparation of the nucleoside monomers is depicted in Scheme 4.

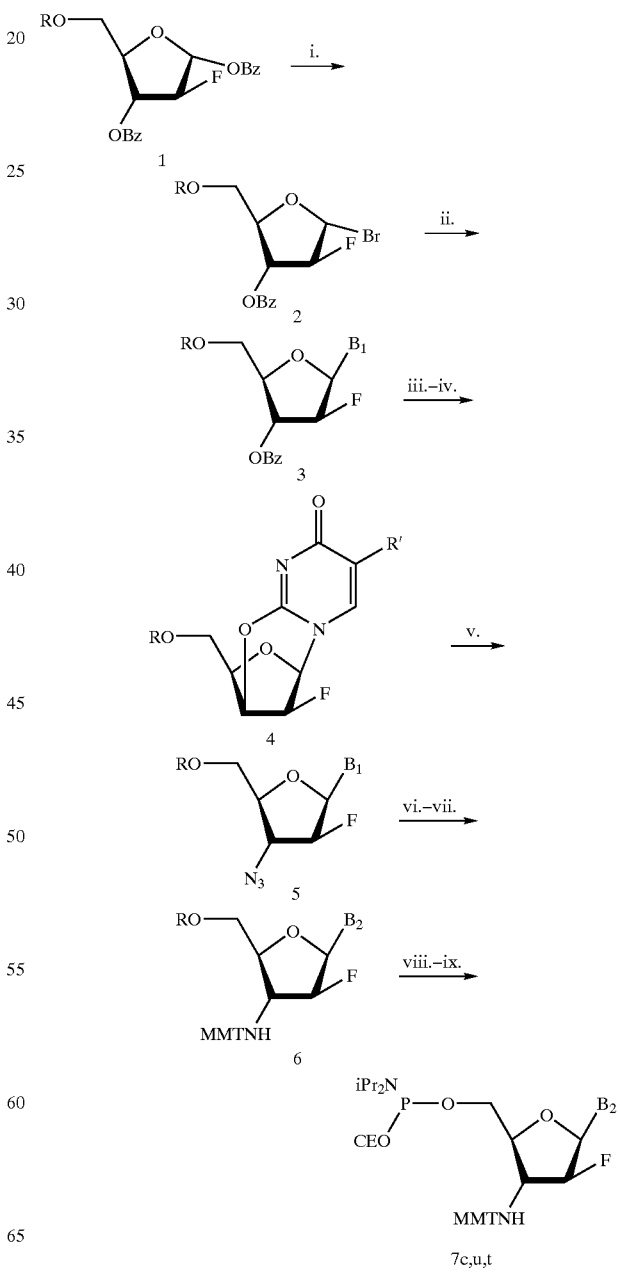

Scheme 4

-continued

B₁ = Thy, Ura
B₂ = Thy, Ura, Cyt$^{Bz}$
R = Toluoyl
R' = H, Me
i. HBr;
ii. TMS-bases, TMSOTf;
iii. NH₃/MeOH;
iv. DIAD, PPH₃, BzOH;
v. LiN₃
vi. H₂/Pd;
vii. MMTCl;
viii. NaOH/EtOH;
ix. CEOPClN(iPr)

Sugar precursor 1 (from Pfanstiehl) was converted into the α-1-bromo intermediate 2 with retention of sugar C-1 configuration. Compound 2 was then used, without isolation, for a S$_N$2-type glycosylation reaction with silylated uracil and thymine bases, which resulted in formation of nucleosides 3. Stereo selectivity of the glycosylation reaction was quite high—more than 90% of the formed nucleoside 3 had the desired β-anomeric configuration, as was judged by $^1$H NMR analysis of the reaction mixture. The pure β-isomer of nucleoside 3 was isolated by crystallization from ethanol. Subsequently, 5'- and 3'-O-benzoyl protecting groups of 3 were removed in near quantitative yields by treatment with methanolic ammonia. The resultant 5'-,3'-hydroxyl groups containing nucleoside product was then converted into the 2,3'-anhydronucleoside 4 under Mitsunobu reaction conditions. The treatment of the 2,3'-anhydronuclesides with lithium azide yielded the key 3'-azido precursor 5. This compound was then converted into phosphoramidites 7t,u by the catalytic reduction of 3'-azido to 3'-amino group by hydrogenation, followed by 3'-tritylation, 5'-O-deprotection and 5'-O-phosphitylation. Cytidine phosphoramidite 7c was obtained from the 3'-azido precursor using the uracil-to-cytosine conversion process. Total yields of the phosphoramidites 7c,t,u were in the range of 8–12% based on the starting sugar precursor 1. Structure of the monomers was confirmed by $^1$H, $^{31}$P, $^{19}$F NMR and by mass spectrometric analysis. Oligonucleotide synthesis using the 2'-arabino-fluoronucleotide monomer was then conducted on an automated DNA/RNA ABI 394 synthesizer as described below.

EXAMPLE 3

Synthesis of Oligonucleotide N3'→P5' Thiophosphoramidates

Oligonucleotide N3'→P5' thiophosphoramidates were prepared by the amidite transfer reaction on an ABI 394 synthesizer. The fully protected monomer building blocks were 3'-aminotrityl nucleoside-5' -(2-cyanoethyl-N,N-diisopropyl) phosphoramidite where nucleoside is 3'-deoxy-thymidine, 2',3'-dideoxy-N$^2$-isobutyryl-guanosine, 2',3'-dideoxy-N$^6$-benzoyl-adenosine or 2',3'-dideoxy-N$^4$-benzoyl-cytidine. 5'-Succinyl-3'-aminotrityl-2',3'-dideoxy nucleosides were coupled with an amino group containing long chain controlled pore glass (LCAA-CPG) and used as the solid support. The synthesis was performed in the direction of 5' to 3'. The following protocol was used for the assembly of oligonucleotide N3'→P5' thiophosphoramidates: (i) detritylation, 3% dichloroacetic acid in dichloromethane; (ii) coupling, 0.1 M phosphoramidite and 0.45 M tetrazole in acetonitrile, 25 sec; (iii) capping, isobutyric anhydride/2,6-lutidine/THF 1/1/8 v/v/v as Cap A and standard Cap B solution; (iv) sulfurization, 15% S$_8$ in carbon disulfide containing 1% triethylamine, 1 min. Before and after the sulfurization step the column was washed with neat carbon disulfide to prevent elemental sulfur precipitation. The oligonucleotide thiophosphoramidates were cleaved from the solid support and deprotected with concentrated aqueous ammonia. The compounds were analyzed and purified by HPLC. Ion exchange (IE) HPLC was performed using DIONEX DNAPac™ ion exchange column at pH 12 (10 mM NaOH) with a 1%/min linear gradient of 10 mM NaOH in 1.5 M NaCl and a flow rate of 1 ml/min. The products were desalted on Sephadex NAP-5 gel filtration columns (Pharmacia) and lyophilized in vacuo. $^{31}$P NMR experiments were performed in deuterium oxide to analyze the extent of sulfurization analysis ($^{31}$P NMR δ, ppm 58, 60 broad signals Rp,Sp isomers).

Oligonucleotide thiophosphoramidate 5'-GTTAGGGTTAG-3' (SEQ ID NO:1) was synthesized the following way: An ABI Model 394 synthesizer was set up with 0.1M solutions of 3'-tritylamino-2',3'-dideoxy-N-benzoyl-adenosine (N$^2$-isobutyryl-guanosine, and thymidine) 5'-(2-cyanoethyl-N,N-diisopropyl) phosphoramidites. The reagent bottle of station #10 was filled with neat carbon disulfide and reagent bottle #15 was filled with a solution of 15% S$_8$ in carbon disulfide containing 1% triethylamine. As the activator the commercially available 0.45 M solution of tetrazole in acetonitrile was used. Cap A solution (station #11) was replaced by tetrahydrofuran/isobutyric anhydride/2,6-lutidine 8/1/1 v/v/v solution. Cap B was also the commercially available reagent. A new function was created to deliver carbon disulfide from station #10 to the column. The default sulfur synthesis cycle was modified the following way: sulfurization time was set at 1 min., and before and after sulfurization carbon disulfide was delivered to the column for 20 s. The synthesis column was filled with 1 μmole solid support N$^2$-isobutyryl-3'-(trityl)amino-2',3'-dideoxyguanosine-5'-succinyl-loaded CPG (controlled pore glass). The sequence of the compound was programmed as GATTGGGATTG (5'→3') (SEQ ID NO:9). The trityl group was removed at end of the synthesis and the column was washed manually with carbon disulfide and acetonitrile. The solid support was removed from the column and treated with 1 ml concentrated aqueous ammonia at 55° C. for 6 hr in a tightly closed glass vial. After filtration most of the ammonia was evaporated and the remaining solution was desalted using Sephadex™ NAP-5 gel filtration columns (Pharmacia) followed by lyophilization in vacuo. The product was analyzed and purified as described above. All of the other thiophosphoramidate oligonucleotides listed in Table 2 (SEQ ID NOs:2–4) were synthesized using the above described methods.

EXAMPLE 4

Acid Stability and Duplex Formation Properties of Oligonucleotide N3'→P5' Thiophosphoramidates Oligonucleotide thiophosphoramidates unexpectedly demonstrated an increased acid stability relative to phosphoramidate counterparts. One might have expected that substitution of the non-bridge oxygen of the internucleotide phosphate group with sulfur should have resulted in a decrease in the acid stability of the phosphoramidate because the difference in the electron-donating properties of sulfur verses oxygen, which could have made the protonation of the 3'-NH easier. However, contrary to this prediction, the thiophosphoramidate internucleotide linkages were found to be more acid stable than their oxo-phosphoramidate counterparts.

The half-lives of thiophosphoramidate TAG$_3$T$_2$AGACA$_2$ (SEQ ID NO:2) and its phosphoramidate counterpart in 40% aqueous acetic acid at room temperature were approximately 6 hours and 0.5 hour, respectively, according to IE HPLC analysis (see Table 1). Moreover, the composition of the hydrolysis products was different between the thiophosphoramidate and its phosphoramidate counterpart. The acid hydrolysis of the thiophosphoramidate appears to initially result in de-sulfurization, rather than cleavage of internucleoside N-P groups, as it occurs for the phosphoramidates. These results indicated a much higher resistance to acidic conditions of the thiophosphoramidates than that of the phosphoramidate oligonucleotides, thus indicating that this new class of thiophosphoramidate oligonucleotides has improved potential for the development of oral oligonucleotide therapeutics as compared to other phosphoramidate oligonucleotides.

TABLE 1

| Expt | Oligomer | Type[a] | Tm, °C.[b] | −Tm, °C.[c] | Acid Stability[d] |
|---|---|---|---|---|---|
| 1. | GTTAGGGTTAG SEQ ID NO:1 | po | 44.2 | — | |
| 2. | TAGGGTTAGACAA SEQ ID NO:2 | po | 45.2 | — | |
| 3. | Same as expt 1 | np | 72.1 | 27.9 | |
| 4. | Same as expt 2 | np | 71.7 | 26.5 | 0.5 hr |
| 5. | Same as expt 1 | nps | 71.5 | 27.3 | |
| 6. | Same as expt 2 | nps | 70.0 | 24.8 | 6 hr |

[a]po, np, nps correspond to phosphodiester, N3'→P5' phosphoramidate and thiophosphoramidate groups, respectively;
[b]melting temperature, Tm (±0.5° C.) of the duplexes formed with a complementary natural RNA oligomer in 150 mM NaCl, 10 mM sodium phosphate buffer pH 7.4;
[c]increase of Tm relative to the natural phosphodiester counterpart;
[d]half-live of oligonucleotide in 40% aqueous acetic acid at room temperature.

Duplex formation properties of oligonucleotide phosphoramidates with complementary RNA strand were evaluated using thermal dissociation experiments. The results are summarized in Table 1. The presented data show that the oligonucleotide thiophosphoramidates formed significantly more stable complexes than the isosequential natural phosphodiester oligomers wherein the difference in Tm was ~25–27° C. per oligomer. Also, the increase in the thermal stability of duplexes was similar to that observed for the phosphoramidate oligomers. This indicates that the substitution of non-bridging oxygen by sulfur atom in internucleoside phosphoramidate group did not alter RNA binding properties of these compounds significantly, which was determined by N-type sugar puckering of the 3'-aminonucleosides and by increased sugar-phosphate backbone hydration.

EXAMPLE 5

Preparation of Affinity Purified Extract Having Telomerase Activity

Extracts used for screening telomerase inhibitors were routinely prepared from 293 cells over-expressing the protein catalytic subunit of telomerase (hTERT). These cells were found to have 2–5 fold more telomerase activity than parental 293 cells. 200 ml of packed cells (harvested from about 100 liters of culture) were resuspended in an equal volume of hypotonic buffer (10 mM Hepes pH 7.9, 1 mM MgCl$_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer 'A' containing 50 mM NaCl. After dialysis the extract was centrifuged for 30 min at 25,000×g. Prior to affinity chromatography, Triton X-100™ (0.5 %), KCl (0.3 M) and tRNA (50 µg/ml) were added. Affinity oligo (5' biotinTEG-biotinTEG-biotinTEG-GTA GAC CTG TTA CCA guu agg guu ag 3' [SEQ ID NO:5]; lower case represents 2' O-methyl ribonucleotides and upper case represents deoxynucleotides) was added to the extract (1 nmol per 10 ml of extract). After an incubation of 10 min at 30° C., Neutravidin beads (Pierce; 250 µl of a 50% suspension) were added and the mixture was rotated overnight at 4° C. The beads were pelleted and washed three times with Buffer 'B' containing 0.3 M KCl, twice with Buffer 'B' containing 0.6 M KCl, and twice more with Buffer B containing 0.3 M KCl. Telomerase was eluted in Buffer 'B' containing 0.3 M KCl, 0.15% Triton X-100™ and a 2.5 molar excess of displacement oligo (5'-CTA ACC CTA ACT GGT AAC AGG TCT AC-3' [SEQ ID NO:6] at 0.5 ml per 125 µl of packed Neutravidin beads) for 30 min. at room temperature. A second elution was performed and pooled with the first. Purified extracts typically had specific activities of 10 fmol nucleotides incorporated/min/µl extract, or 200 nucleotides/min/mg total protein.

| Buffer 'A' | Buffer 'B' |
|---|---|
| 20 mM Hepes pH 7.9 | 20 mM Hepes pH 7.9 |
| 1 mM MgCl2 | 1 mM EDTA |
| 1 mM DTF | 1 mM DTT |
| 1 mM EGTA | 10% glycerol |
| 10% glycerol | 0.5 Triton X-100 ™ |

EXAMPLE 6

Telomerase Inhibition by Oligonucleotide N3'→P5' Thiophosphoramidates

Three separate 100 µl telomerase assays are set up with the following buffer solutions: 50 mM Tris acetate, pH 8.2, 1 mM DTT, 1 mM EGTA, 1 mM MgCl$_2$, 100 mM K acetate, 500 µM dATP, 500 µM TTP, 10 µM [$^{32}$P-]dGTP (25 Ci/mmol), and 100 nM d(TTAGGG)$_3$ [SEQ ID NO:7]. To the individual reactions 2.5, 5 or 10 µl of affinity-purified telomerase (see Example 4) is added and the reactions are incubated at 37° C. At 45 and 90 minutes, 40 µl aliquots are removed from each reaction and added to 160 µl of Stop Buffer (100 mM NaCl, 10 mM Na pyrophosphate, 0.2% SDS, 2 mM EDTA, 100 µg/ml tRNA). 10 µl trichloroacetic acid (TCA) (100%) is added and the sample is incubated on ice for 30 minutes. The sample is pelleted in a microcentrifuge (12000×g force) for 15 minutes. The pellet is washed with 1 ml 95% ethanol and pelleted again in the microcentrifuge (12000×g force) for 5 minutes. The pellet is resuspended in 50 µl dH$_2$O and transferred to a 12×75 glass test tube containing 2.5 ml of ice cold solution of 5% TCA and 10 mM Na pyrophosphate. The sample is incubated on ice for 30 minutes. The sample is filtered through a 2.5 cm wet (dH$_2$O) GFC membrane (S&S) on a vacuum filtration manifold. The filter is washed three times under vacuum with 5 ml ice cold 1% TCA, and once with 5 ml 95% ethanol. The filter is dried and counted in a scintillation counter using scintillation fluid. The fmol of nucleotide incorporated is determined from the specific activity of radioactive tracer. The activity of extract is calculated based on the DNTP incorporated and is expressed as fmol dNTP/min/µl extract.

Telomerase Activity Assay
Bio-Tel FlashPlate Assay

An assay is provided for the detection and/or measurement of telomerase activity by measuring the addition of TTAGGG telomeric repeats to a biotinylated telomerase substrate primer; a reaction catalyzed by telomerase. The biotinylated products are captured in streptavidin-coated microtiter plates. An oligonucleotide probe complementary to 3.5 telomere repeats labeled with $^{33}P$ is used for measuring telomerase products, as described below. Unbound probe is removed by washing and the amount of probe annealing to the captured telomerase products is determined by scintillation counting.

Method:
20. Thiophosphoramidate oligonucleotides were stored as concentrated stocks and dissolved in PBS.
21. For testing, the thiophosphoramidate oligonucleotides were diluted to a 15×working stock in PBS and 2 µl was dispensed into two wells of a 96-well microtiter dish (assayed in duplicate).
22. Telomerase extract was diluted to a specific activity of 0.04–0.09 fmol dNTP incorporated/min./µl in Telomerase Dilution Buffer and 18 µl added to each sample well to preincubate with compound for 30 minutes at room temperature.
23. The telomerase reaction was initiated by addition of 10 µl Master Mix to the wells containing telomerase extract and oligonucleotide compound being tested. The plates were sealed and incubated at 37° C. for 90 min.
24. The reaction was stopped by the addition of 10 µl HCS.
25. 25 µl of the reaction mixture was transferred to a 96-well streptavidin-coated FlashPlate™ (NEN) and incubated for 2 hours at room temperature with mild agitation.
26. The wells were washed three times with 180 µl 2×SSC without any incubation.
27. The amount of probe annealed to biotinylated telomerase products were detected in a scintillation counter.

Buffers:
Telomerase Dilution Buffer
50 mM Tris-acetate, pH 8.2
1 mM DTT
1 mM EGTA
1 mM $MgCl_2$
830 nM BSA
Master Mix (MM)
50 mM Tris-acetate, pH 8.2
1 mM DTT
1 mM EGTA
1 mM $MgCl_2$
150 mM K acetate
10 µM dATP
20 µM dGTP
120 µM dTTP
100 nM biotinylated primer (5'-biotin-AATCCGTCGAGCAGAGTT-3') [SEQ ID NO:8]
5.4 nM labeled probe [5'-CCCTA ACCCTAACCCTAACCC-($^{33}P$) $A_{1-50}$-3'] [SEQ ID NO:9]; specific activity approximately $10^9$ cpm/µg or higher Hybridization Capture Solution (HCS)
12×SSC (1X =150 mM NaCl/30 mM $Na_3$Citrate)
40 mM EDTA
40 mM Tris-HCl, pH 7.0

Using the foregoing assay, the thiophosphoramidate oligonucleotides represented by SEQ ID NO:1 and SEQ ID NO:2 were shown to have telomerase $IC_{50}$ values below 1.0 nM (see TABLE 2, Experiments 1 and 3).

TABLE 2

EVALUATION OF OLIGOS 1–4 AS TELOMERASE INHIBITORS IN COMPARISON WITH PHOSPHORAMIDATES:

| EXP | Oligonucleotide | $IC_{50}$(nM) phosphor-amidate | $IC_{50}$(nM) thiophosphor-amidate |
|---|---|---|---|
| 20. | 5'-GTTAGGGTTAG-3' SEQ ID NO:1 | 1.9 | 0.89 |
| 21. | 5'-GTTGAGTGTAG-3' SEQ ID NO:3 | 1000 | 177.4 |
| 22. | 5'-TAGGGTTAGACAA-3' SEQ ID NO:2 | 1.64 | 0.41 |
| 23. | 5'-TAGGTGTAAGCAA-3' SEQ ID NO:4 | 1000 | 79.3 |

Oligonucleotide sequence 2 (SEQ ID NO:3) is a mismatch control for the oligonucleotides used in experiment 1 (SEQ ID NO:1). Similarly, oligonucleotide sequence 4 (SEQ ID NO:4) is a mismatch control for the oligonucleotides (SEQ ID NO:2) used in Experiment 3.

The telomerase inhibition data presented in Table 2 show that the thiophosphoramidate polynucleotides of the present invention are about 2–3 times better at inhibiting telomerase activity relative to counterpart phosphoramidates oligonucleotides. Thus, the inventive thiophosphoramidate oligonucleotides are not only more active in the telomerase inhibition assay, as compared to their phosphoramidate counterparts, but are also more acid resistant than them as well. This combination of characteristics imparts the inventive thiophosphoramidate oligonucleotides with an important advantage compared to phosphoramidate polynucleotides.

EXAMPLE 7

Anti-tumor Activity of Thiophosphoramidate Oligonucleotides

Ex vivo Studies
a. Reduction of Telomere Length in Tumor Cells

Colonies of human breast epithelial cells (spontaneously immortalized) were prepared using standard methods and materials. Colonies were prepared by seeding 15-centimeter dishes with about $10^6$ cells in each dish. The dishes were incubated to allow the cell colonies to grow to about 80% confluence, at which time each of the colonies were divided into two groups. One group was exposed to a subacute dose of thiophosphoramidate polynucleotide SEQ ID NO:2 at a predetermined concentration (e.g., between about 100 nM and about 20 µM) for a period of about 4–8 hours after plating following the split. The second group of cells were similarly exposed to mismatch control oligonucleotide SEQ ID NO:4.

Each group of cells is then allowed to continue to divide, and the groups are split evenly again (near confluence). The same number of cells were seeded for continued growth. The test thiophosphoramidate oligonucleotide or control oligonucleotide was added every fourth day to the samples at the same concentration delivered initially. In one experiment the cells were additionally treated with FuGENE6™ (Boehringer-Mannhiem) following manufacturers instructions. FuGENE6™ enhances oligonucleotide uptake by the cells.

Figure 4:
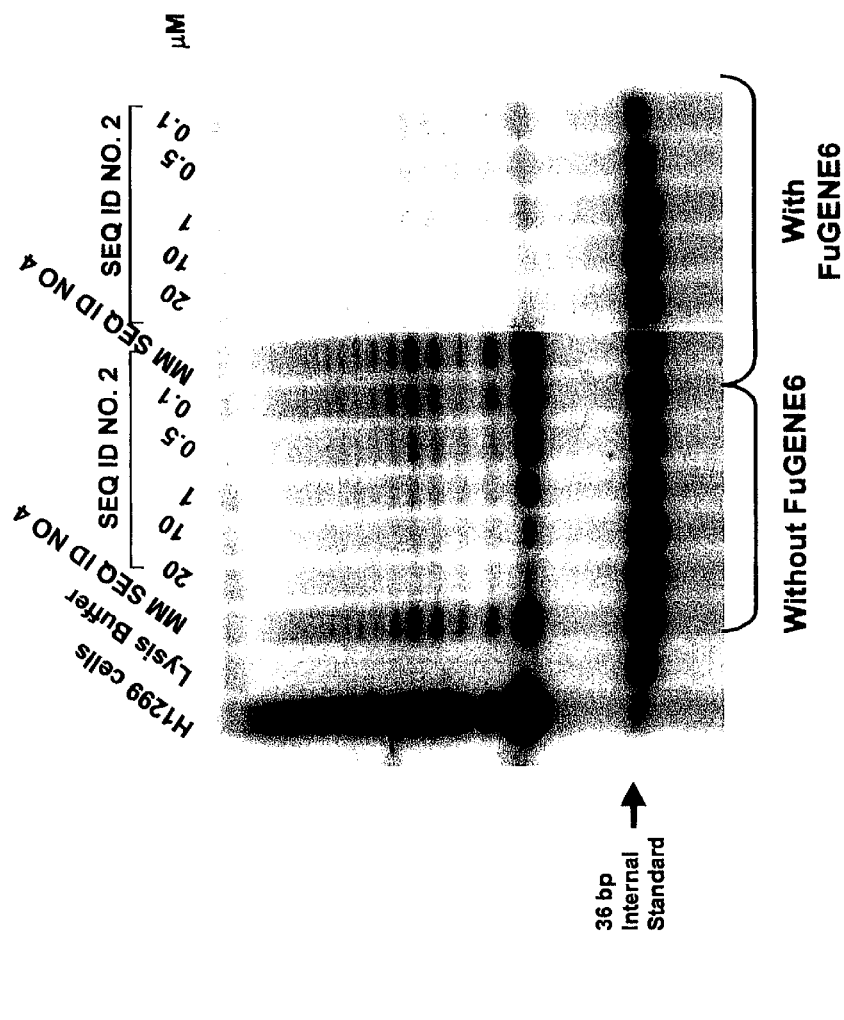
FIG. 4 shows the results of an in vitro telomerase inhibition assay performed using increasing amount of thiophosphoramidate oligonucleotide of SEQ ID NO:2 that is complementary to telomerase RNA, or SEQ ID NO:4 that contains nucleotide mismatches.
Figure 5:
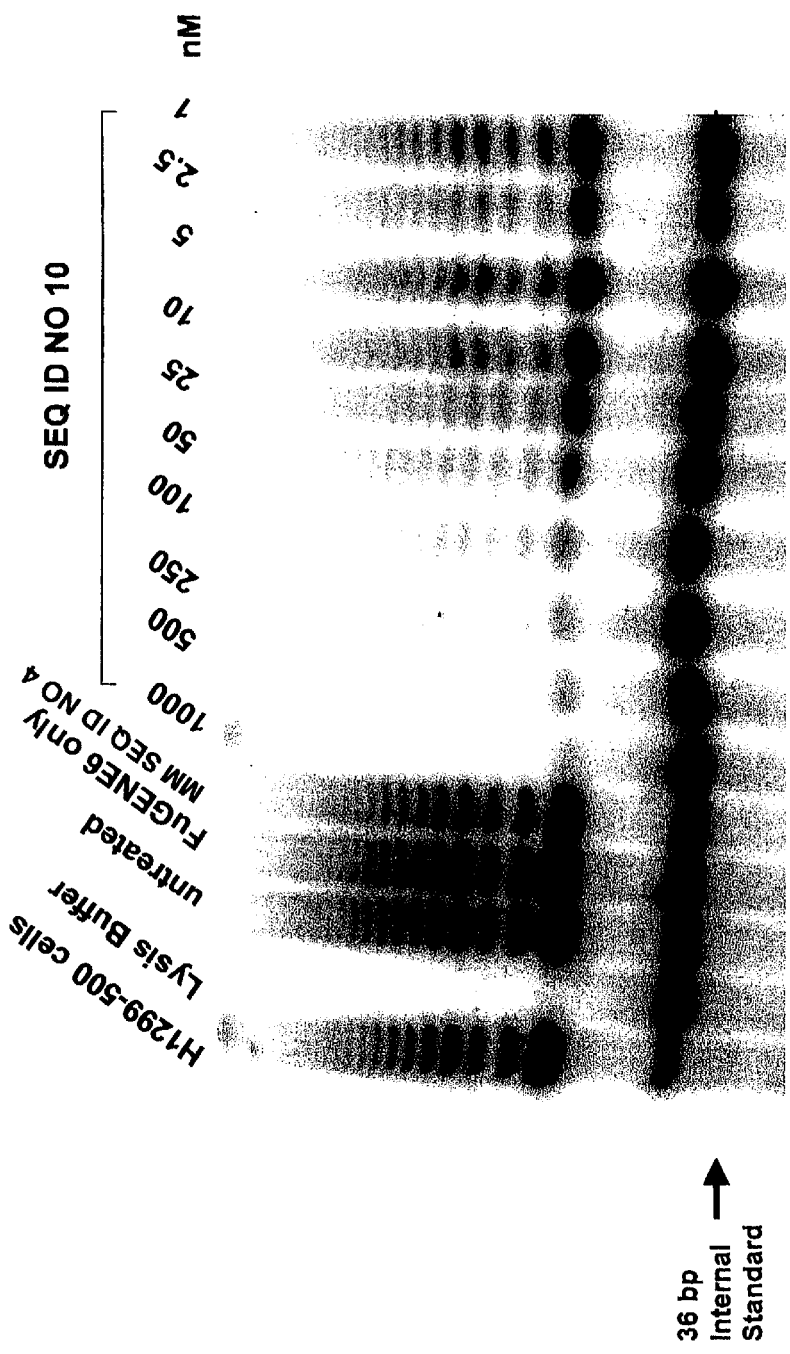
FIG. 5 shows the results of an in vitro telomerase inhibition assay performed using increasing amount of thiophosphoramidate oligonucleotide of SEQ ID NO:8 that is complementary to telomerase RNA.

Telomere length was determined by digesting the DNA of the cell samples using restriction enzymes specific for sequences other than the repetitive $T_2AG_3$ sequence of human telomeres (TRF analysis). The digested DNA was separated by size using standard techniques of gel electrophoresis to determine the lengths of the telomeric repeats, which appear, after probing with a telomere DNA probe, on the gel as a smear of high-molecular weight DNA (approximately 2 Kb–15 Kb). FIGS. 4 and 5 show examples of such experiments.

The results presented in FIG. 4 indicate that the thiophosphoramidate oligonucleotide SEQ ID NO:2 is a potent in vitro inhibitor of telomerase activity. In the absence of FuGENE6™, the thiophosphoramidate oligonucleotide SEQ ID NO:2 induced a large decrease in telomere length when incubated with HME50-5E cells in the range of 1–20 $\mu$M. When cells were coincubated with FuGENE6 and thiophosphoramidate oligonucleotide SEQ ID NO:2 telomere size was reduced compared to the control cells at even the lowest concentration tested (100 nM).

The results presented in FIG. 5 indicate that the thiophosphoramidate oligonucleotide having the sequence CAGTTAGGGTTAG (SEQ ID NO:8) is a potent in vitro inhibitor of telomerase activity. When the cells were incubated with the thiophosphoramidate oligonucleotide SEQ ID NO:8, telomere size was reduced compared to the control cells at even the lowest concentration tested (1 nM). Thus, the inventive thiophosphoramidate oligonucleotides are potent in vitro inhibitors of telomerase activity in immortalized human breast epithelial cell.

Figure 6:
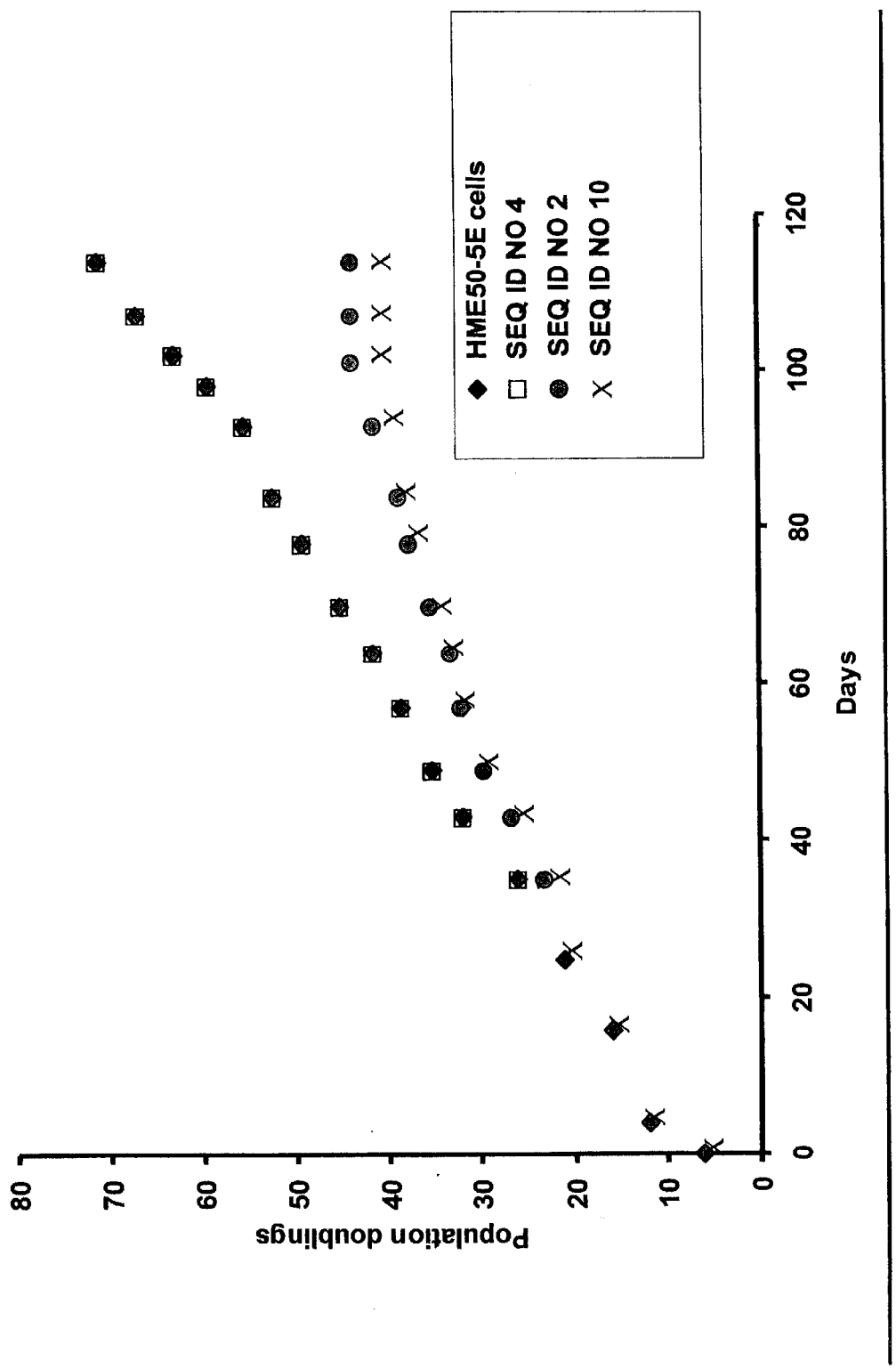
FIG. 6 shows the results of SEQ ID NOs:2 and 8 that are complementary to telomerase RNA, and SEQ ID NO:4 that contains nucleotide mismatches on the growth of HME50-5E cells.

In another experiment, HME50-5E cells were incubated with one of the thiophosphoramidate polynucleotides shown in SEQ ID NOs:2 and 8. The mismatch oligonucleotide SEQ ID NO:4 was used as a control. All polynucleotides were used at concentrations between about 0.1 $\mu$M and about 20 $\mu$M using the protocol described above. The data on cell growth, shown in FIG. 6, indicates that the cell entered crisis (i.e., the cessation of cell function) within about 100 days following administration of the test thiophosphoramidate oligonucleotides of the invention.

Figure 7:
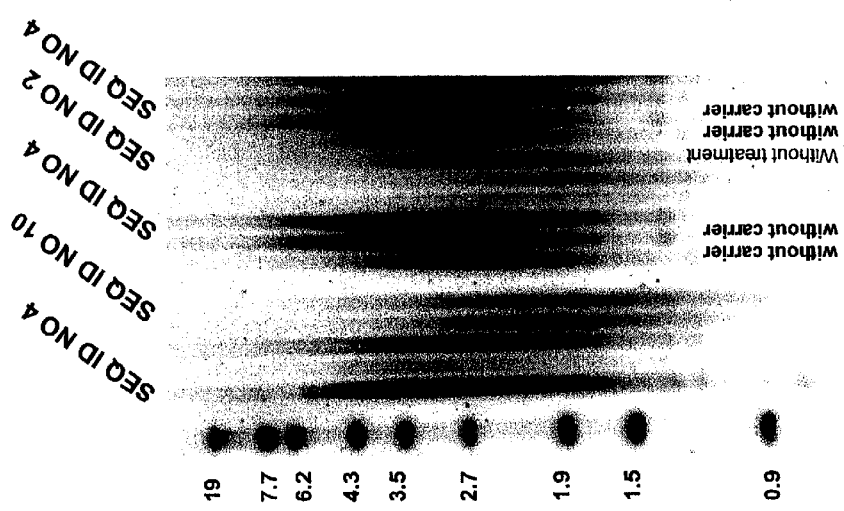
FIG. 7 shows the results of the thiophosphoramidate oligonucleotides on the telomere length of HME50-5E cells.

In addition, TRF analysis of the cells (FIG. 7) using standard methodology shows that the test thiophosphoramidate oligonucleotides of the invention were effective in reducing telomere length. The HME50-5E cells were incubated with one of the thiophosphoramidate polynucleotides shown in SEQ ID NOs:2 and 8. The mismatch oligonucleotide SEQ ID NO:4 was used as a control. All polynucleotides were used at a concentration of about 0.5 $\mu$M using the protocol described above. The length of the telomeres were measured at 10, 20, 40 and 80 days. For the cells with the control mismatch oligonucleotide, the telomere length was measured at day 90, and this data point served as the end point. In addition to the HME50-5E cells described above, this assay can be performed with any telomerase-positive cell line, such as HeLa cells or HEK-293 cells.

b. Specificity

Thiophosphoramidate polynucleotides of the invention are screened for activity ($IC_{50}$) against telomerase and other enzymes known to have RNA components by performing hybridization tests or enzyme inhibition assays using standard techniques. Oligonucleotides having lower $IC_{50}$ values for telomerase as compared to the $IC_{50}$ values toward the other enzymes being screened are said to possess specificity for telomerase.

c. Cytotoxicity

The cell death (XTT) assay for cytotoxicity was performed using HME50-5E, Caki-1, A431, ACHN, and A549 cell types. The cell lines used in the assay were exposed to the thiophosphoramidate oligonucleotide of SEQ ID NO:2 for 72 hours at concentrations ranging from about 1 $\mu$M to about 100 $\mu$M in the presence and absence of lipids. During this period, the optical density (OD) of the samples was determined for light at 540 nanometers (nm). The $IC_{50}$ values obtained for the various cell types (shown in FIG. 8) were generally less than 1 $\mu$M. Thus, no significant cytotoxic effects are expected to be observed at concentrations less than about 100 $\mu$M. It will be appreciated that other tumor cells lines such as the ovarian tumor cell lines OVCAR-5 and SK-OV-3 can be used to determine cytotoxicity in addition to control cell lines such as normal human BJ cells. Other assays for cytotoxicity such as the MTT assay (see Berridge et al., Biochemica, 4:14–19, 1996) and the alamarBlue™ assay (U.S. Pat. No. 5,501,959) can be used as well.

Preferably, to observe any telomerase inhibiting effects the thiophosphoramidate oligonucleotides should be administered at a concentration below the level of cytotoxicity. Nevertheless, since the effectiveness of many cancer chemotherapeutics derives from their cytotoxic effects, it is within the scope of the present invention that the thiophosphoramidate oligonucleotides of the present invention be administered at any dose for which chemotherapeutic effects are observed.

In vivo Animal Studies

A human tumor xenograft model in which OVCAR-5 tumor cells are grafted into nude mice can be constructed using standard techniques and materials. The mice are divided into two groups. One group is treated intraperitoneally with a thiophosphoramidate oligonucleotides of the invention. The other group is treated with a control comprising a mixture of phosphate buffer solution (PBS) and an oligonucleotide complementary with telomerase RNA but has at least a one base mismatch with the sequence of telomerase RNA. The average tumor mass for mice in each group is determined periodically following the xenograft using standard methods and materials.

In the group treated with a thiophosphoramidate oligonucleotide of the invention, the average tumor mass is expected to increase following the initial treatment for a period of time, after which time the tumor mass is expected to stabilize and then begin to decline. Tumor masses in the control group are expected to increase throughout the study. Thus, the thiophosphoramidate oligonucleotides of the invention are expected to lessen dramatically the rate of tumor growth and ultimately induce reduction in tumor size and elimination of the tumor.

Thus, the present invention provides novel thiophosphoramidate oligonucleotides and methods for inhibiting telomerase activity and treating disease states in which telomerase activity has deleterious effects, especially cancer. The thiophosphoramidate oligonucleotides of the invention provide a highly selective and effective treatment for malignant cells that require telomerase activity to remain immortal; yet, without affecting non-malignant cells.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An oligonucleotide comprising a sequence of nucleoside subunits joined by N3'→P5' thiophosphoramidate intersubunit linkages, wherein the oligonucleotide comprises a sequence selected from the group consisting of:
   GTTAGGGTTAG (SEQ ID NO:1);
   TAGGGTTAGACAA (SEQ ID NO:2); and
   CAGTTAGGGTTAG (SEQ ID NO:8)
   and wherein the N3'→P5' thiophosphoramidate intersubunit linkages have the structure 3'-[—NH—P(=O)(—SR)—O—]-5', wherein R is selected from the group consisting of hydrogen, alkyl, and aryl; and pharmaceutically acceptable salts thereof.

2. An oligonucleotide according to claim 1 wherein the oligonucleotide comprises the following sequence: GTTAGGGTTAG (SEQ I.D. No. 1).

3. An oligonucleotide according to claim 1 wherein the oligonucleotide comprises the following sequence: TAGGGTTAGACAA (SEQ I.D. No. 2).

4. An oligonucleotide according to claim 1 wherein the oligonucleotide comprises the following sequence: CAGTTAGGGTTAG (SEQ I.D. No. 8).

5. A pharmaceutical composition comprising a N3'→P5' thiophosphoramidate oligonucleotide according to claim 1 formulated in a pharmaceutically acceptable excipient.

6. A pharmaceutical composition according to claim 5 wherein the oligonucleotide comprises the following sequence: GTTAGGGTTAG (SEQ I.D. No. 1).

7. A pharmaceutical composition according to claim 5 wherein the oligonucleotide comprises the following sequence: TAGGGTTAGACAA (SEQ I.D. No. 2).

8. A pharmaceutical composition according to claim 5 wherein the oligonucleotide comprises the following sequence: CAGTTAGGGTTAG (SEQ I.D. No. 8).

9. A method of inhibiting telomerase enzyme activity, comprising contacting the telomerase enzyme with an oligonucleotide according to claim 1.

10. A method of inhibiting telomerase enzyme activity, comprising contacting the telomerase enzyme with a pharmaceutical composition according to claim 5.

11. A method of inhibiting proliferation of a cell that expresses telomerase, comprising contacting the cell with an oligonucleotide according to claim 1.

12. A method of inhibiting proliferation of a cell that expresses telomerase, comprising contacting the cell with a pharmaceutical composition according to claim 5.

13. A method of formulating a pharmaceutical composition, comprising combining an oligonucleotide according to claim with a pharmaceutically acceptable excipient.

14. A pharmaceutical composition according to claim 5 further comprising a liposome carrier to facilitate cellular uptake of the oligonucleotide.

15. A method according to claim 13, further comprising combining the oligonucleotide, before or after combination with the excipient, with a liposome carrier to facilitate cellular uptake of the oligonucleotide.

16. The method of claim 11 wherein the cell that expresses telomerase is a cell in vitro.

17. The method of claim 11 wherein the cell that expresses telomerase is a cell in a subject.

18. The method of claim 17 wherein the cell is a cancer cell having telomerase activity.

19. A method of inhibiting proliferation of a cancer cell having telomerase activity in a subject, the method comprising administering to the subject an oligonucleotide according to claim 1.

* * * * *

UNITED STATES PATENT AND TRADEMARK OFFICE
CERTIFICATE OF CORRECTION

| | | |
|---|---|---|
| PATENT NO. | : 6,608,036 B1 | Page 1 of 1 |
| APPLICATION NO. | : 09/657445 | |
| DATED | : August 19, 2003 | |
| INVENTOR(S) | : Gryaznov et al. | |

It is certified that error appears in the above-identified patent and that said Letters Patent is hereby corrected as shown below:

In the claims:

At column 40, claim number 13, line number 59, delete "to claim with" and replace with -- to claim 1 with --.

Signed and Sealed this
Tenth Day of November, 2015

Michelle K. Lee
*Director of the United States Patent and Trademark Office*